United States Patent
Patil et al.

(10) Patent No.: US 9,629,919 B2
(45) Date of Patent: *Apr. 25, 2017

(54) DRUG DELIVERY OF TEMOZOLOMIDE FOR SYSTEMIC BASED TREATMENT OF CANCER

(71) Applicant: CEDARS-SINAI MEDICAL CENTER, Los Angeles, CA (US)

(72) Inventors: Rameshwar Patil, Los Angeles, CA (US); Eggehard Holler, Los Angeles, CA (US); Keith L. Black, Los Angeles, CA (US); Julia Y. Ljubimova, Studio City, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,266

(22) Filed: Feb. 26, 2016

(65) Prior Publication Data

US 2016/0175450 A1 Jun. 23, 2016

Related U.S. Application Data

(63) Continuation of application No. 14/179,195, filed on Feb. 12, 2014, now Pat. No. 9,320,807, which is a continuation of application No. 13/513,145, filed as application No. PCT/US2010/059919 on Dec. 10, 2010, now Pat. No. 8,785,371.

(60) Provisional application No. 61/285,495, filed on Dec. 10, 2009.

(51) Int. Cl.
| | |
|---|---|
| A61K 47/48 | (2006.01) |
| C07K 16/28 | (2006.01) |
| C07K 16/30 | (2006.01) |
| A61K 31/4188 | (2006.01) |
| A61K 31/425 | (2006.01) |

(52) U.S. Cl.
CPC ........ *A61K 47/482* (2013.01); *A61K 31/4188* (2013.01); *A61K 31/425* (2013.01); *A61K 47/48061* (2013.01); *A61K 47/48215* (2013.01); *A61K 47/48246* (2013.01); *A61K 47/48338* (2013.01); *A61K 47/48384* (2013.01); *A61K 47/48561* (2013.01); *A61K 47/48584* (2013.01); *A61K 47/48623* (2013.01); *A61K 47/48669* (2013.01); *A61K 47/48692* (2013.01); *C07K 16/2881* (2013.01); *C07K 16/3015* (2013.01); *C07K 16/3053* (2013.01); *C07K 2317/24* (2013.01); *C07K 2317/77* (2013.01)

(58) Field of Classification Search
None
See application file for complete search history.

(56) References Cited

U.S. PATENT DOCUMENTS

| | | |
|---|---|---|
| 7,935,677 B2 | 5/2011 | Ljubimova et al. |
| 8,309,614 B2 | 11/2012 | Ding et al. |
| 2005/0187206 A1 | 8/2005 | Adin et al. |
| 2007/0259008 A1 | 11/2007 | Ljubimova et al. |
| 2009/0263331 A1 | 10/2009 | Wu et al. |

FOREIGN PATENT DOCUMENTS

WO 2009126913 A1 10/2009

OTHER PUBLICATIONS

D.N. Louis, H. Ohgaki, et al. The 2007 WHO classification of tumours of the central nervous system. Acta Neuropathol. 114:97-109 (2007).
2009 CBTRUS Statistical Report: Primary Brain and Central Nervous System Tumors Diagnosed in the united States in 2004-2005. http://www.cbtrus.org/reports/2009-NPCR-04-05/CBTRUS-NPCR2004-2005-Report-.pdf (accessed Nov. 17, 2009).
A.R. Asthagiri, et al. Advances in brain tumor surgery. Neurol Clin. 25:975-1003 (2007).
W. Stummer, et al. Fluorescence-guided surgery with 5-aminolevulinic acid for resection of malignant glioma: a randomised controlled multicentre phase III trial. Lancet Oncol. 7:392-401 (2006).
M. Lacroix, et al. A multivariate analysis of 416 patients with glioblastoma multiforme: prognosis, extent of resection, and survival. J Neurogurg. 95:190198 (2001).
Arrowsmith, et al. Part 39 synthesis of bis(imidazotetrazine)s with saturated spacer groups. J Chem Soc Perkin Trans 1. 24:4432-4438 (2000).
R. Stupp, et al. Radiotherapy plus concomitant and adjuvant temozolomide for glioblastma. N Engl J Med. 352:987-996 (2005).
N. Auger, et al. Genetic alterations associated with acquired with temozolide resistance in SNB-19, a human glioma cell line. Mol Cancer Ther. 5:2182-2192 (2006).

(Continued)

*Primary Examiner* — Robert A Wax
*Assistant Examiner* — Randeep Singh
(74) *Attorney, Agent, or Firm* — Wilson Sonsini Goodrich & Rosati

(57) ABSTRACT

The present invention relates to methods of drug delivery for the treatment of a condition or disease, such as cancer. In one embodiment, the invention provides a method of preparing a multifunctional nanoconjugate of temozolomide (TMZ) by conjugating TMZ in its hydrazide form to a polymalic acid platform. In another embodiment, the polymalic acid platform is conjugated to a monoclonal antibody to transferrin receptor, a trileucine (LLL) moiety, and/or a polyethylene glycol (PEG) moiety. The present invention relates to methods of drug delivery for the treatment of a condition or disease, such as cancer. In one embodiment, the invention provides a method of preparing a multifunctional nanoconjugate of temozolomide (TMZ) by conjugating TMZ in its hydrazide form to a polymalic acid platform. In another embodiment, the polymalic acid platform is conjugated to a monoclonal antibody to transferrin receptor, a trileucine (LLL) moiety, and/or a polyethylene glycol (PEG) moiety.

9 Claims, 13 Drawing Sheets

(56) References Cited

OTHER PUBLICATIONS

C.C. Chen, et al. Of *Escherichia coli* and man: understanding glioma resistance to temozolmide therapy. In E. G. Meir (eds.), CNS Cancer, Humana Press, Atlanta, 2009, pp. 679-711.

G.J. Kitange, et al. Induction of MGMT expression is associated with temozolomide resistance in glioblastoma kenografts. Neuro Oncol. 11:281-291 (2009).

R. Stachi-Fainaro, et al. Targeting angiogenesis with a conjugate of HPMA copolymer and TNP-470. Nat Med. 10:255-261 (2004).

R. Duncan. The dawning era of polymer therapeutics. Nat Rev Drug Discov. 2:347-360 (2003).

S.V. Vinogradov, et al. Mixed polymer micelles of amphiphilic and cationic copolymers for delivery of antisense oligonucleotides. J Drug Target 12:517-526 (2004).

A.V. Kabanov, et al. Polymer genomics: shifting the gene and drug delivery paradigms. J Control Release. 101:259-271 (2005).

D. Peer, et . Nanocarriers as an emerging platform for cancer therapy. Nat Nanotechnol. 2:751-760 (2007).

M. Ferrari. Cancer nanotechnology: opportunities and challenges. Nat Rev Cancer. 5:161-171 (2005).

A. Nori, et al. Intracellular targeting of polymer-bound drugs for cancer chemotherapy. Adv Drug Deliv Rev. 57:609-636 (2005).

R. Duncan, et al. Polymer-drug conjugates: towards a novel approach for the treatment of endrocine-related cancer. Endocr Relat Cancer. 12:S189-S199 (2005).

H. Maeda, et al. Vascular permeability enhancement in solid tumor: various factors, mechanisms involved and its Implications. Int Immunopharmacol. 3:319-328 (2003).

M. Fujita, et al. Brain tumor tandem targeting using a combination of monoclonal antibodies attached to biopoly (b-L-malic acid). J Control Release. 122:356-363 (2007).

B.S. Lee, et al. Polycefin, a new prototype of a multifunctional nanoconjugate based on poly(b-L-malic acid) for drug delivery. Bioconjug Chem. 17:3170326 (2006).

E. Segal, and R. Satchi-Fainaro. Design and development of polymer conjugates as anti-angiogenic agents. Adv Drug Deliv Rev. 61:1159-1176 (2009).

S. Brem, et al. Local delivery of temozolomide by biodegradable polymers is superior to oral administration in a rodent glioma model. Cancer Chemother Pharmacol. 60:643-650 (2007).

U. Akbar, et al. Delivery of temozolomide to the tumor bed via biodegradable gel matrices in a novel model of Intracranial glioma with resection. J. Neurooncol. 94:203-212 (2009).

L.X. Zhao, et al. Synthesis and antitumour activities of 3-substituted 4-oxo-3 H-imidazo [5,1-d][1,2,3,5] tetrazine-8-carboxylic acids and their derivatives. Chin J Med Chem. 11:263-269 (2001).

E. Holler, Poly(malic acid) from natural sources. In N.P. Cheremisinoff (eds.), Handbook of Engineering Polymeric Materials, Marcel Dekker, New York, 1997, pp. 93-103.

J. Carlsson, et al. Protein Thiolation and reversible protein-protein conjugation. N-Succinimidyl 3-(2-pyridyldithio) priopionate, a new heterobifunctional reagent. Biochem J. 173:723-737 (1978).

J.Y. Ljubimova, et al. Poly(malic acid) nanoconjugates containing various antibodies and oligonucleotides for multitargeting drug delivery delivery. Nanomedicine. 3:247-265 (2008).

F.N. Fu, al. et al Calcein permeability of liposomes mediated by type A botulinum neurotoxin and its light and heavy chains. J. Protein Chem. 18:701-707 (1999).

T.J. Mosmann. Rapid colorimetric assays for cellular growth and survival: application to proliferation and cytotoxicity assays. Immunol Methods. 65:55-63 (1983).

H.S. Friedman, et al. Temozolomide and treatment of malignant glioma. Clin Cancer Res. 6:2585-2597 (2000).

R.N. Trivedi, et al. Human methyl purine DNA glycosylase and DNA polymerase b expression collectively predict sensitivity to temozolomide. Mol Pharmacol. 74:505-516 (2008).

A.E. Nel, et al. Understanding biophysicochemical interactions at the nano-bio interface. Nat Mater. 8:543-557 (2009).

M.R. Lorenz, et al. Uptake of functionalized, fluorescent-labeled polymeric particles in different cell lines and stem cells. Biomaterials. 27:2820-2828 (2006).

D.E. Owens, et al. Opsonization, biodistribution, and pharmacokinetics of polymeric nanoparticles. Int J Pharm. 307:93-102 (2006).

Extended European Search Report dated Oct. 19, 2013 in counterpart European Patent Application No. 10836765.7.

Braun, et al. Treatment glioblastoma multiforme cells with temozolomide-BioShuttle ligated by the inverse Diels-Alder ligation chemistry. Drug Design, Development and Therapy, Dove Medical Press Ltd, UK, vol. 2008, No. 2, 289-301 (2009).

Waldeck, et al. TMZ-BioShuttle—A reformulated temozolomide. International Journal of Medical Sciences, Ivyspring International Publisher, Lake Haven, AU, vol. 5, No. 5,273-284 (2008).

Rameshwar, et al. Temozolomide Delivery to Tumor Cells by a Multifunctional Nano Vehicle Based on Ply (l-L-malic acid). Pharmaceutical Research, Kluwer Academic Publishers-Plenum Publishers, NL, vol. 27, No. 11, 2317-2329 (2010).

DRUG DELIVERY OF TEMOZOLOMIDE FOR SYSTEMIC BASED TREATMENT OF CANCER

CROSS REFERENCE TO RELATED APPLICATIONS

This application is a continuation of U.S. patent application Ser. No. 14/179,195, which was filed on Feb. 12, 2014. U.S. patent application Ser. No. 14/179,195 is a continuation of U.S. patent application Ser. No. 13/513,145, which was filed on Aug. 8, 2012 and issued on Jul. 22, 2014 as U.S. Pat. No. 8,785,371. U.S. patent application Ser. No. 13/513,145 is a 35 U.S.C. §371 national phase application of International Application No. PCT/US2010/059919, which was filed on Dec. 10, 2010, and claimed priority to U.S. Provisional Patent Application No. 61/285,495, filed Dec. 10, 2009. All of the above applications are incorporated by reference herein as if fully set forth.

STATEMENT REGARDING FEDERALLY SPONSORED RESEARCH OR DEVELOPMENT

This invention was made with government support under Grant No. CA123495 awarded by National Institutes of Health. The government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Malignant gliomas are the most common (60-70%) of all CNS/brain tumors. Annually there are approximately 5 cases of malignant gliomas per 100,000 people and over 14,000 new cases are diagnosed each year in the United States (1, 2). Surgery remains the standard therapy for primary brain tumors. Although surgery may be combined with radiation therapy and/or followed with chemotherapy to destroy remaining cancer cells, patients still have a poor survival advantage (3-5). In recent years, the prodrug Temozolomide (TMZ, TEMODAR), for example, which undergoes spontaneous conversion to the active alkylating agent, has emerged as a potent chemotherapeutic agent (6). In combination with radiotherapy, it has been shown to substantially increase median survival compared with radiotherapy alone (7). However, as with many potential chemotherapeutic agents, TMZ has considerable toxicity, which prevents therapeutic dosage increase. Moreover, another limiting factor of TMZ treatment is tumor resistance to the drug (8-10).

Thus, there is a need in the art for novel drug delivery systems that have tumor targeting, increased solubility, enhanced accumulation in solid tumors, decreased general toxicity, increased maximum tolerated doses, circumvention of multidrug resistance and enhanced apoptosis induction.

SUMMARY OF THE INVENTION

Various embodiments include a drug delivery system comprising a polymalic acid platform conjugated to a pro-drug, and one or more targeting antibodies, a trileucine (LLL) moiety, and/or a polyethylene glycol (PEG) moiety. In another embodiment, the pro-drug comprises a therapeutically effective amount of a compound of the formula:

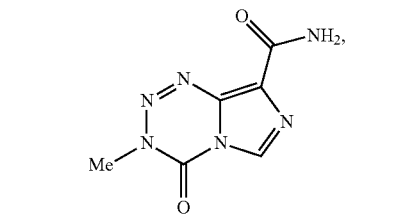

(Formula 1)

or a pharmaceutical equivalent, analog, derivative and/or salt thereof. In another embodiment, the one or more targeting antibodies is a monoclonal antibody to transferrin receptor (TfR). In another embodiment, the polymalic acid platform comprises a compound of the formula:

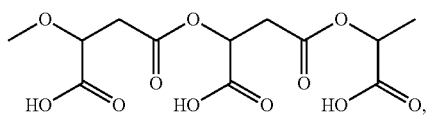

(Formula 2)

or a pharmaceutical equivalent, analog, derivative and/or salt thereof. In another embodiment, the one or more targeting antibodies is a anti-TfR humanized antibody. In another embodiment, the anti-TfR humanized antibody is used for active transport to a tumor. In another embodiment, one or more targeting antibodies is an anti-TfR mouse monoclonal antibody and/or an anti-TfR human monoclonal antibody.

Other embodiments include a pharmaceutical composition, comprising a therapeutically effective amount of a multifunctional nanoconjugate of temozolmide (TMZ), and a pharmaceutically acceptable carrier. In another embodiment, the multifunctional nanoconjugate of TMZ is a compound of the formula:

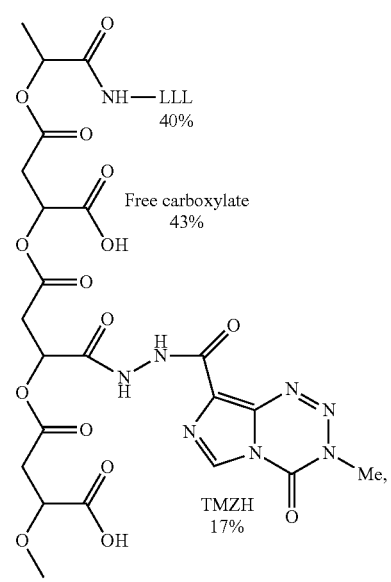

(Formula 3)

or a pharmaceutical equivalent, analog, derivative and/or salt thereof. In another embodiment, the multifunctional nanoconjugate of TMZ is a compound of the formula:

(Formula 4)

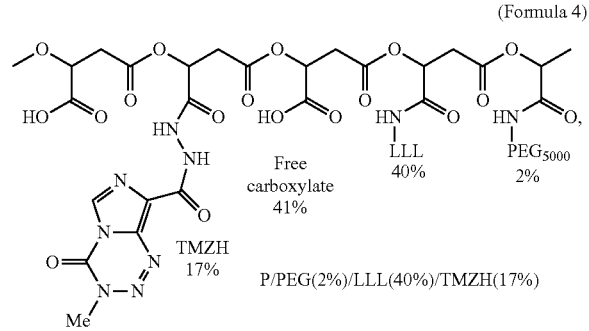

P/PEG(2%)/LLL(40%)/TMZH(17%)

or a pharmaceutical equivalent, analog, derivative and/or salt thereof.

Other embodiments include a method of treating a disease and/or condition in an individual, comprising administering a therapeutically effective dosage of a drug delivery system comprising a polymalic acid platform conjugated to a pro-drug, and one or more targeting antibodies, a trileucine (LLL) moiety, and/or a polyethylene glycol (PEG) moiety to the individual, and treating the individual. In another embodiment, the pro-drug comprises a therapeutically effective amount of a compound of the formula:

(Formula 1)

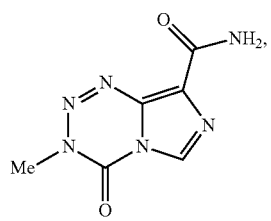

or a pharmaceutical equivalent, analog, derivative and/or salt thereof. In another embodiment, the therapeutically effective amount of the compound of the formula:

(Formula 1)

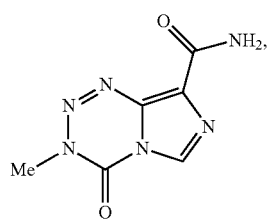

or a pharmaceutical equivalent, analog, derivative and/or salt thereof, is between 1 mg/kg and 10 mg/kg concentration. In another embodiment, the targeting antibody is a monoclonal antibody to transferrin receptor (TfR). In another embodiment, the polymalic acid platform comprises a compound of the formula:

(Formula 2)

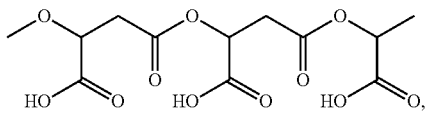

or a pharmaceutical equivalent, analog, derivative and/or salt thereof. In another embodiment, the drug delivery system comprises a compound of the formula:

(Formula 3)

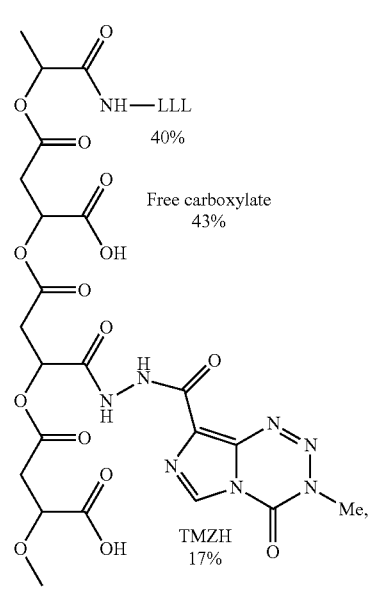

or a pharmaceutical equivalent, analog, derivative and/or salt thereof. In another embodiment, the drug delivery system comprises a compound of the formula:

(Formula 4)

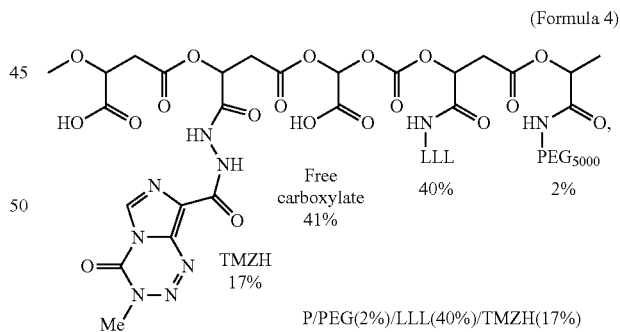

P/PEG(2%)/LLL(40%)/TMZH(17%)

or a pharmaceutical equivalent, analog, derivative and/or salt thereof. In another embodiment, the drug delivery system is administered to the individual intravenously. In another embodiment, the drug delivery system is administered to the individual at a concentration of about 4 mg/kg. In another embodiment, the drug delivery system is administered to the individual by direct injection and/or orally. In another embodiment, the drug delivery system is administered to the individual at a concentration of 75 mg/m$^2$. In another embodiment, the individual is a human. In another embodiment, the individual is a mouse and/or rat. In another embodiment, the drug delivery system comprises an anti-TfR mouse monoclonal antibody and/or an anti-TfR human monoclonal antibody. In another embodiment, the drug delivery system comprises an anti-TfR humanized antibody.

Various embodiments include a method of preparing a drug delivery system, comprising:
conjugating a compound of the formula:

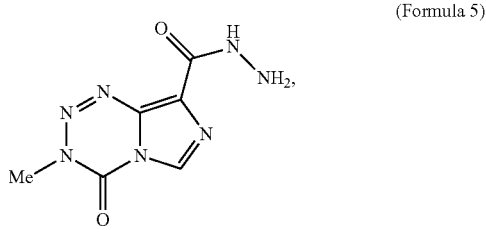 [SMILES: Cn1nnc2c(C(=O)NN)ncn2c1=O]

(Formula 5)

or a pharmaceutical equivalent, analog, derivative and/or salt thereof, to an ionic polymalic acid. In another embodiment, the ionic polymalic acid comprises one or more targeting antibodies, a trileucine (LLL) moiety, and/or a polyethylene glycol (PEG) moiety. In another embodiment, the ionic polymalic acid comprises an anti-TfR humanized antibody for transporting to a tumor.

Other features and advantages of the invention will become apparent from the following detailed description, taken in conjunction with the accompanying drawings, which illustrate, by way of example, various embodiments of the invention.

DESCRIPTION OF THE INVENTION

Figure 1:
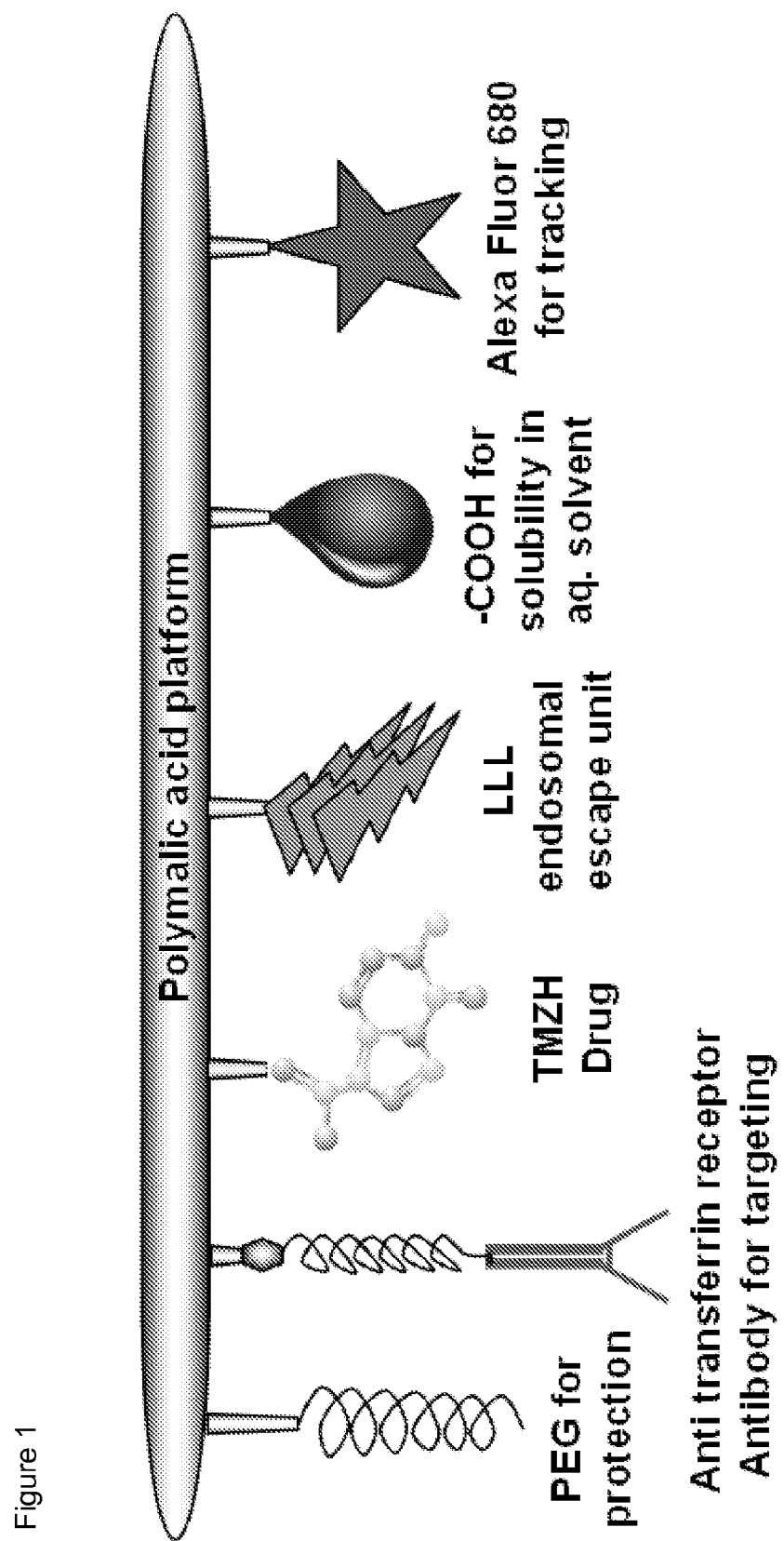
FIG. 1 depicts, in accordance with an embodiment herein, schematic presentation of the drug delivery system.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "TMZ" also refers to temozolomide, and is a compound of the formula:

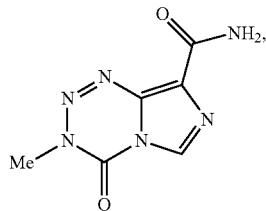
(Formula 1)

or a pharmaceutical equivalent, analog, derivative and/or salt thereof.

As used herein, the term "TMZH" also refers to temozolomide hydrazide, and is a compound of the formula:

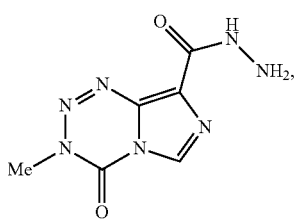
(Formula 5)

or a pharmaceutical equivalent, analog, derivative and/or salt thereof.

As used herein, the term "PMLA" is an abbreviation for poly(β-L-malic acid), and is a compound of the formula:

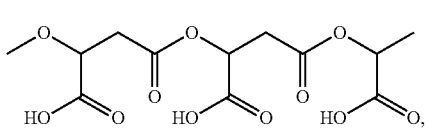
(Formula 2)

or a pharmaceutical equivalent, analog, derivative and/or salt thereof.

As used herein, the term "HuTfR mAb" means anti-human transferrin receptor monoclonal antibody.

As used herein, the term "LOEt" means L-leucine ethyl ester.

As used herein, the term "LLL" is an abbreviation of L-Leu-(L-Leu)-(L-Leu).

As used herein, the term "Alex680" means the fluorescent dye ALEXA FLUOR 680 C2 maleimide.

As used herein, the term "PMLA-LLL" includes PMLA containing LLL, which is conjugated by amide bond involving the N-terminal —$NH_2$.

As used herein, the term "PMLA-LLL40%" includes PMLA containing 40% of pendant carboxylates (100%) conjugated by amide bond involving the N-terminal —$NH_2$ of oligopeptide trileucine LLL.

As used herein, the term "Polycefin" is a general name for therapeutic nanoconjugates based on polymalic acid for drug delivery. It may contain multifunctional components, such as a drug, a targeting moiety, and an endosome escaping unit.

As disclosed herein, temozolomide (TMZ) is a pro-drug releasing a DNA alkylating agent that may treat glial tumors when combined with radiation. TMZ is toxic and therapeutic dosages are limited by severe side effects. Targeted delivery is thus needed to improve efficiency and reduce non-tumor tissue toxicity. The inventors synthesized multifunctional targetable nanoconjugates of TMZ hydrazide using a poly (β-L-malic acid) platform, which contained a targeting monoclonal antibody to transferrin receptor (TfR), trileucine (LLL) for pH-dependent endosomal membrane disruption, and PEG for protection.

In one embodiment, the present invention provides a composition comprising a multifunctional nanoconjugate of temozolomide (TMZ), or a pharmaceutical equivalent, analog, derivative, or salt thereof. In another embodiment, the multifunctional nanoconjugate of TMZ, or a pharmaceutical equivalent, analog, derivative, or salt thereof, comprises TMZ conjugated to an ionic polymalic acid. In another embodiment, the TMZ, or pharmaceutical equivalent, analog, derivative, or salt thereof comprises TMZ hydrazide. In another embodiment, the ionic polymalic acid comprises poly(β-L-malic acid). In another embodiment, the poly(β-L-malic acid) contains a targeting moiety, a pH-dependent endosome membrane disruption moiety, and/or a PEG moiety. In another embodiment, the targeting moiety comprises a targeting monoclonal antibody to transferrin receptor. In another embodiment, the endosome membrane disruption moiety comprises trileucine (LLL) and/or L-leucine ethyl ester (LoEt).

As further disclosed herein, the water-soluble TMZ nanoconjugates had hydrodynamic diameters in the range of 6.5 to 14.8 nm and potentials in the range of −6.3 to −17.7 mV. 50% degradation in human plasma was observed in 40 h at 37° C. TMZ conjugated with polymer had a half-life of 5-7 h, compared with 1.8 h for free TMZ. The strongest reduction of human brain and breast cancer cell viability was obtained by versions of TMZ nanoconjugates containing LLL and anti-TfR antibody. TMZ-resistant cancer cell lines were sensitive to TMZ nanoconjugate treatment. TMZ-polymer nanoconjugates entered the tumor cells by receptor-mediated endocytosis, effectively reduced cancer cell viability, and can be used for targeted tumor treatment.

In one embodiment, the present invention provides a method of treating a cancer by administering a therapeutically effective dosage of a composition comprising a multifunctional nanoconjugate of temozolomide (TMZ), or a pharmaceutical equivalent, analog, derivative, or salt thereof, to an individual. In another embodiment, the multifunctional nanoconjugate of temozolomide (TMZ), or a pharmaceutical equivalent, analog, derivative, or salt thereof, is administered to the individual systemically. In another embodiment, the multifunctional nanoconjugate of temozolomide (TMZ), or a pharmaceutical equivalent, analog, derivative, or salt thereof, is administered to the individual systemically via intravenous administration. In another embodiment, the multifunctional nanoconjugate of temozolomide (TMZ), or a pharmaceutical equivalent, analog, derivative, or salt thereof, is administered to the individual orally and/or via direct injection. In another embodiment, the cancer is brain cancer. In another embodiment, side effects to the individual are minimized due to less free diffusion of the TMZ, wherein the TMZ is conjugated to a polycefin platform. In another embodiment, side effects to the individual are minimized to the individual due to specific tumor treatment and targeting resulting a homing device moiety of the multifunctional nanoconjugate of TMZ.

In conjunction with various embodiments described herein, the inventors have successfully conjugated TMZ via the hydrazide bond to the highly negatively charged PMLA that renders the prodrug no longer diffusible through membranes. This allows a highly more potent and effective delivery of TMZ (or other drugs). Unlike the conjugated TMZ form, the more traditional orally applied TMZ for treating human gliomas has the potency to be distributed all over the entire organism. After penetration of the lipophilic prodrug through membranes into the cytoplasm of recipient cells it will be activated by the hydrolytic mechanism described herein. The active drug is then ready to methylate proteins and especially DNA, guanine at N7 position, followed by methylation of adenine at the O3 position and of guanine at the O6 position (33). Failure of repair will drive these cells into apoptosis. Hydrolytic activation of the prodrug at sites other than the cytoplasm is inefficient due to the fact that the cationic methyl diazonium like any other charged molecule cannot passively penetrate membranes. However, in contrast, by conjugating TMZ and rendering the prodrug no longer diffusible through the membranes, the active methyl diazonium cation can only be generated from the nanodrug. Free passive diffusion of the PMLA conjugate into recipient cells is highly unlikely because of its high negative charge, and generation of active drug outside the cytoplasm would not be effective due to its own intrinsic charge. Therefore, the nanodrug can only give rise to nucleic acid methylation if it is internalized into the cytoplasm of recipient cells.

As further disclosed herein, a multifunctional nanoconjugate, or a pharmaceutical equivalent, analog, derivative, or salt thereof, was synthesized with PMLA as the platform and prodrug TMZ in its hydrazide form, $H_2N$-Leu-Leu-LeuOH (LLL) or $NH_2$-LeuOEt (LOEt) for disruption of endosomal membrane, antibodies for targeting, and PEG against resorption and enzyme degradation.

In one embodiment, the present invention provides a method of preparing a multifunctional nanoconjugate of temozolomide (TMZ), or a pharmaceutical equivalent, analog, derivative, or salt thereof by conjugating TMZ in its hydrazide form to a polycefin platform. In another embodiment, the multifunctional nanoconjugate of TMZ is prepared by the following steps, or a combination thereof: (1) chemical activation of the PMLA pendant carboxyl groups forming the NHS-ester and subsequently the nucleophilic replacement by forming stable amide bonds; (2) conjugation of antibodies via thioether bond formation, where because of the PMLA chain length inhomogeneity, an excess of mAb is chosen in order to increase the likelihood that at least one molecule was conjugated with each polymer chain; (3) conjugation with LLL, where because the amount of 40% of carboxyl groups conjugated with LLL for most efficient membrane disruption activity limits the amount of TMZH conjugation to 17%, in order to increase the amount of TMZH loading, (4) carboxyl activation is repeated after conjugation with LLL, (5) before conjugation with TMZH.

The present invention is also directed to a kit for materials for preparing a multifunctional nanoconjugate of temozolomide (TMZ), as well as the administration of the multifunctional nanoconjugate of TMZ to the individual, and may include a polymalic acid platform, PEG for protection, antibodies for targeting, TMZ molecules in hydrazide form, COOH for solubility in aqueous solvent, and tracking molecules such as the fluorescent dye ALEXA FLUOR 680, and combinations thereof. The kit is an assemblage of materials or components, including at least one of the inventive compositions.

The exact nature of the components configured in the inventive kit depends on its intended purpose. For example, some embodiments are configured for the purpose of treating brain cancer or drug delivery in mammalian subjects, such as, but not limited to, human subjects, farm animals, domestic animals, and laboratory animals.

Instructions for use may be included in the kit. "Instructions for use" typically include a tangible expression describing the technique to be employed in using the components of the kit to effect a desired outcome, such as to prepare a multifunctional nanoconjugate of TMZ and to deliver a therapeutically effective dosage of TMZ to an individual. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in preparing a nanoconjugate. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a solution of multifunctional nanoconjugate of TMZ or components thereof. The packaging material generally has an external label which indicates the contents and/or purpose of the kit and/or its components.

In various embodiments, the present invention provides pharmaceutical compositions including a pharmaceutically acceptable excipient along with a therapeutically effective amount of Polycefin-LLL. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to an intravenous injection, aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of an effective delivery of a multifunctional nanoconjugate of TMZ, or a pharmaceutical equivalent, analog, derivative, or salt thereof, can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

As described herein, various embodiments of the invention include the therapeutically effective delivery of a multifunctional nanoconjugate of TMZ, or a pharmaceutical equivalent, analog, derivative, or salt thereof, to an individual in treatment of brain cancer. As readily apparent to one of skill in the art, the invention may be applied to any number of targets where it would be beneficial to deliver a drug or molecule to an individual while decreasing side effects due to less free diffusion and/or targeted delivery. Similarly, any number of conditions and/or diseases may be beneficially treated and the invention is in no way limited to treatment of brain cancer and/or tumor suppression. For example, various embodiments described herein may include the treatment of HIV and/or AIDS, and any other number of conditions where it is advantageous to deliver a therapeutically effective dosage of a drug. Finally, as would be readily apparent to one of skill in the art, various molecules and/or drugs may also be delivered, including the delivery of proteins, and the various embodiments described herein are in no way limited to delivery of TMZ, or its pharmaceutical equivalent, analog, derivative, or salt thereof.

Various embodiments of the invention may also be practiced in conjunction with an overall treatment regimen. For example, as described herein, various embodiments include the delivery of TMZ by way of disruption of the endosome. As readily apparent to one of skill in the art, additional drugs or substances that were previously inactive in the endosome will then become active upon the disruption of the endosome. Thus, various embodiments of the invention may include additional drugs or substances administered to the subject being treated and the invention is not only limited to drugs and/or molecules covalently linked to the scaffold as described herein. Similarly, as readily apparent to one of skill in the art, various embodiments of the invention may be used in conjunction with or in combination with additional therapeutics.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General

Temozolomide (TMZ) is a pro-drug releasing a DNA alkylating agent that may treat glial tumors when combined with radiation. TMZ is toxic and therapeutic dosages are limited by severe side effects. Targeted delivery is thus needed to improve efficiency and reduce non-tumor tissue toxicity. The inventors synthesized multifunctional targetable nanoconjugates of TMZ hydrazide using a poly(β-L-malic acid) platform, which contained a targeting monoclonal antibody to transferrin receptor (TfR), trileucine (LLL) for pH-dependent endosomal membrane disruption, and PEG for protection.

As further disclosed herein, the water-soluble TMZ nanoconjugates had hydrodynamic diameters in the range of 6.5 to 14.8 nm and potentials in the range of −6.3 to −17.7 mV. 50% degradation in human plasma was observed in 40 h at 37° C. TMZ conjugated with polymer had a half-life of 5-7 h, compared with 1.8 h for free TMZ. The strongest reduction of human brain and breast cancer cell viability was obtained by versions of TMZ nanoconjugates containing LLL and anti-TfR antibody. TMZ-resistant cancer cell lines were sensitive to TMZ nanoconjugate treatment. TMZ-polymer nanoconjugates entered the tumor cells by receptor-mediated endocytosis, effectively reduced cancer cell viability, and can be used for targeted tumor treatment.

Example 2

Reagents Used

TMZ was purchased from AK Scientific, Inc. (Mountain View, Calif., USA). TMZ hydrazide (TMZH) was synthesized from TMZ as described (25). Mouse anti-human TfR mAb RVS10 was purchased from Southern Biotech (Birmingham, Ala., USA). PMLA (100 kDa; polydispersity 1.3; hydrodynamic diameter 6.6 nm; ζ potential −22.5 mV, pH 7.5 at 25° C.) was obtained from culture broth of *Physarum polycephalum* as described (26). mPEG$_{5000}$-amine and maleimide-PEG$_{3400}$-maleimide were obtained from Laysan Bio, Inc. (Arab, Ala., USA). NH$_2$-Leu-OEt (LOEt) and NH$_2$-Leu-Leu-Leu-OH (LLL) were purchased from Bachem Americas, Inc. (Torrance, Calif., USA). Egg yolk and phosphatidylcholine from Fluka (Buchs, Switzerland). 3-(2-Pyridyldithio)-propionate (PDP) was synthesized as described (27). The fluorescent dye ALEXA FLUOR 680 C2 maleimide (Alex680) was from Invitrogen Corporation (Carlsbad, Calif., USA). Unless otherwise indicated, all chemicals and solvents of highest purity were purchased from Sigma-Aldrich (St. Louis, Mo.) USA.

Example 3

Analytical Methods for Chemical Synthesis

The conjugation reaction of PMLA with PEG, TMZH, LLL and LOEt was followed by thin layer chromatography (TLC) on precoated silica gel 60 F254 aluminum sheets (Merck, Darmstadt, Germany) and visualization of spots by UV light and/or by ninhydrin staining. The concentration of free or conjugated TMZH was monitored by reading A$_{328}$ and using known amounts of TMZ or TMZH standards. Size exclusion chromatography was performed on LACHROM ELITE, an analytical High Performance Liquid Chromatograph (HPLC) system with Diode Array Detector L 2455 (Hitachi, Pleasanton, Calif., USA), and M$_w$ was measured using BioSep-SEC-S 3000 (300×7.80 mm) (Phenomenex, Torrance, Calif., USA) with 50 mM sodium phosphate buffer pH 6.8 and polystyrene sulfonates as molecular weight standards. Thiol residues attached to PMLA were assayed by the method of Ellman. Enzyme-linked immunosorbent assay (ELISA) was used to determine the functional activity of conjugated antibody using a Protein Detector ELISA Kit (KPL, Inc., Gaithersburg, Mass., USA). Human TfR ectodomain used as antigen was obtained from Protein Expression Center, California Institute of Technology, Pasadena, USA.

Example 4

Syntheses of Nanoconjugates

Figure 10:
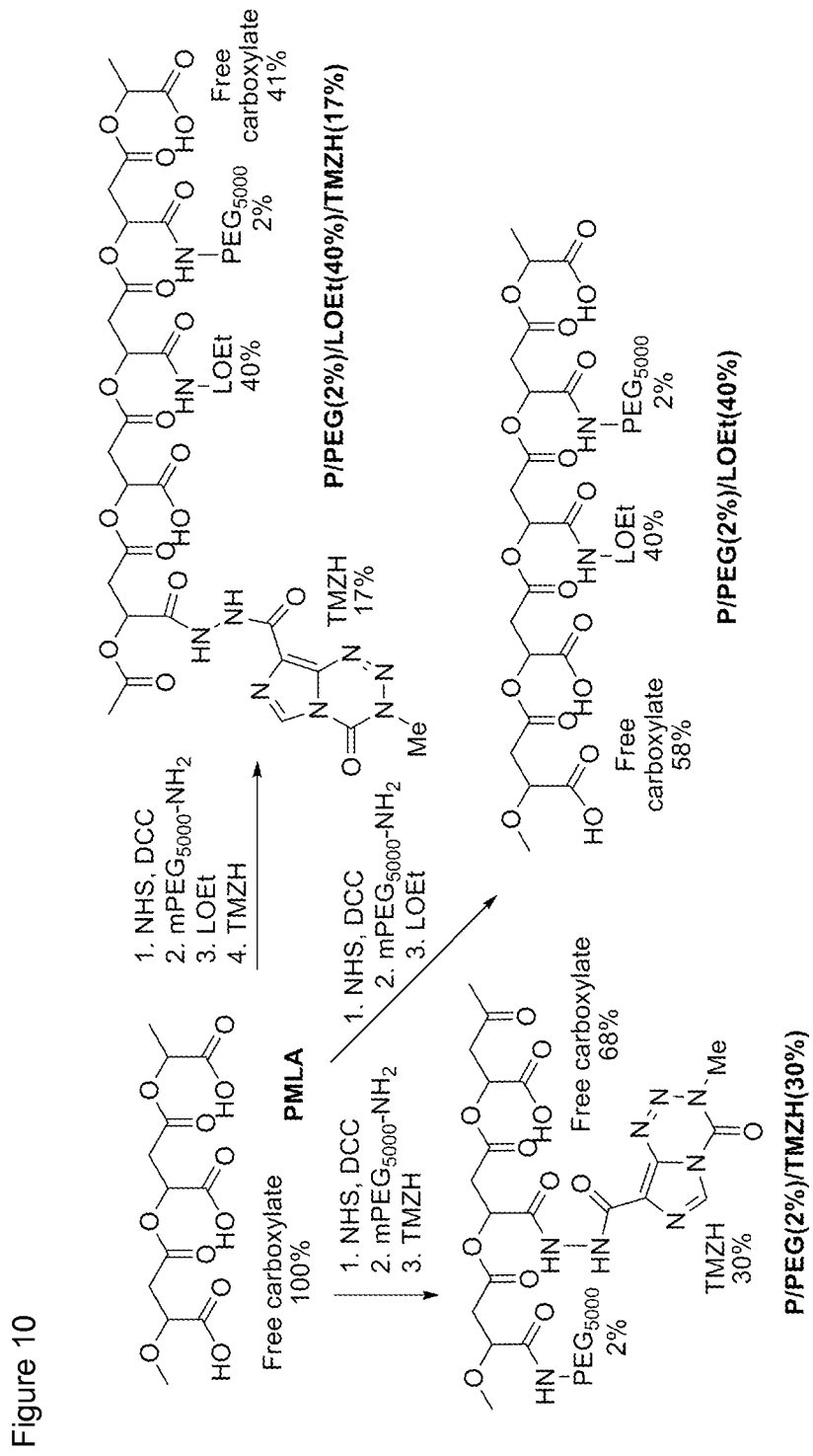
FIG. 10 depicts, in accordance with an embodiment herein, synthetic strategy for LOEt conjugates containing TMZH.
Figure 11:
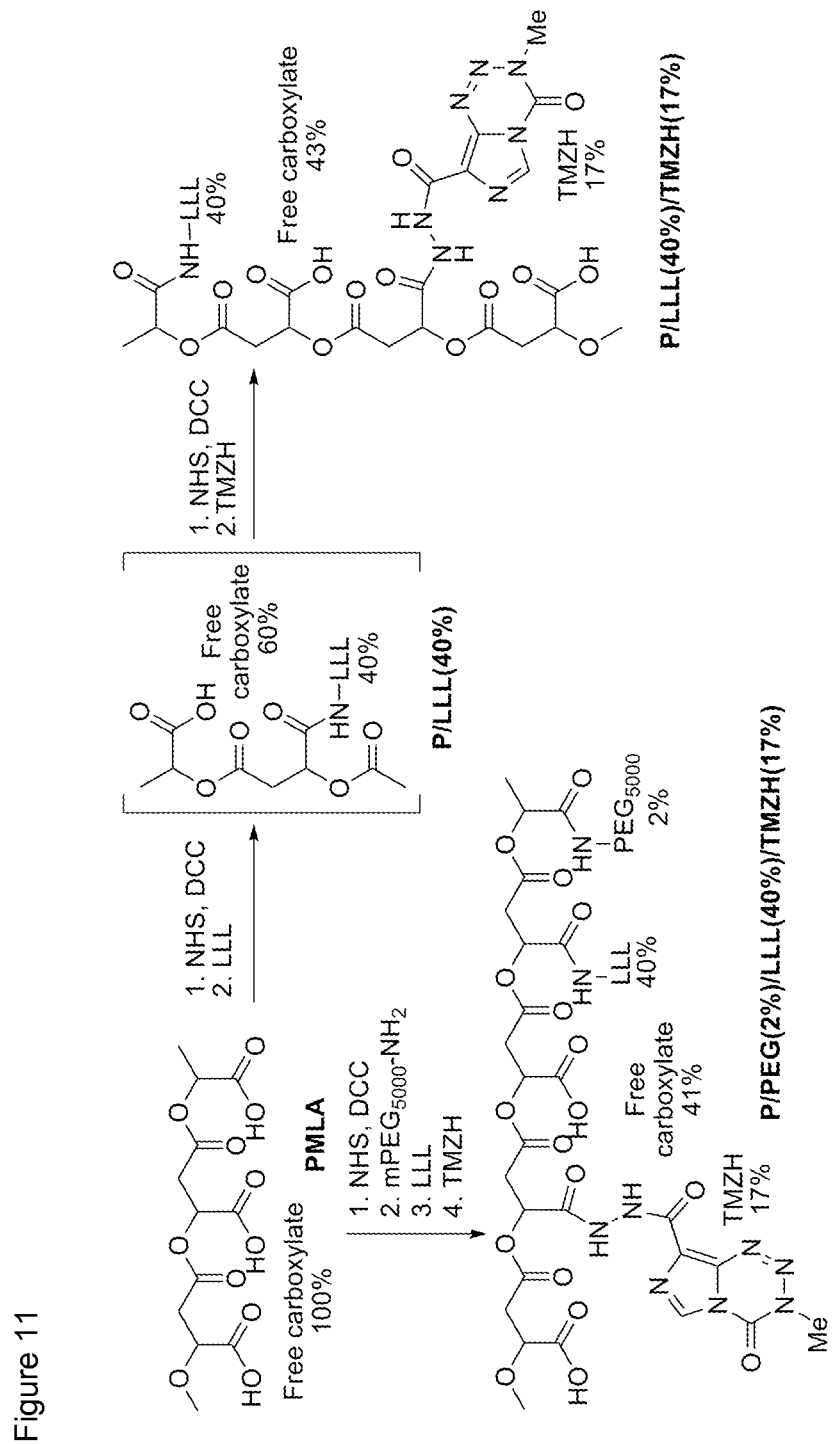
FIG. 11 depicts, in accordance with an embodiment herein, synthetic strategy for LLL conjugates containing TMZH.

A variety of conjugates were synthesized in order to examine the effect of each conjugated functional group on membrane disruption and cell viability. Two membrane disrupting units were examined for their usefulness in endosome escape: LOEt and LLL. The synthetic strategies for the nanoconjugates containing the LOEt endosomal escape unit are summarized in FIG. 10 and for those containing LLL endosomal escape unit, in FIG. 11. Conjugates containing different amounts of TMZH were synthesized by analogous methods.

Example 5

Conjugate P/PEG(2%)/TMZH(30%)

N-Hydroxysuccinimide (NHS) (1 mmol) and N,N'-dicyclohexylcarbodiimide DCC (1 mmol) dissolved in 2 ml of DMF were added consecutively to the solution of 116 mg of PMLA (1 mmol with regard to malyl units) dissolved in 1 ml of anhydrous acetone under vigorous stirring at room temperature (RT). The reaction mixture became turbid almost immediately upon addition of the NHS/DCC mixture indicating the formation of dicyclohexylurea. After stirring at RT for 3 h to complete the activation of carboxyl groups, 0.02 mmol of mPEG$_{5000}$-NH$_2$ (in 0.5 ml of DMF, 2 Mol-% with regard to malyl units) was added followed by 0.02 mmol of triethylamine (TEA). After the reaction was completed according to TLC/ninhydrin test, the reaction mixture was filtered and most of the solvent was removed by rotary evaporation. Next, 0.3 mmol of TMZH (15 mg/ml in DMF, 30 Mol-% with regard to malyl units) was added drop-wise at RT under stirring followed by 0.3 mmol of TEA. The reaction was complete within 2 h according to TLC (Rf=0.4 for TMZH; Rf=0 for the polymer conjugate; chloroform: methanol 9:1; visualization under UV and by ninhydrin). Addition of 5-6 ml 100 mM sodium phosphate buffer containing 150 mM NaCl (pH 6.0) to the reaction mixture was followed by 30 min stirring at RT. After centrifugation at 1500×g for 10 min the clear supernatant was passed over a SEPHADEX column (PD-10, GE Healthcare, Piscataway, N.J., USA) pre-equilibrated with deionized (DI) water. The product containing fractions were collected and conjugate P/PEG(2%)/TMZH(30%) was obtained after freeze drying.

Example 6

Conjugate P/PEG(2%)/LOEt(40%)/TMZH(17%)

PMLA activation and conjugation of PEG followed the method described for conjugate P/PEG(2%)/TMZH(30%). A solution of LOEt hydrochloride (200 mM in DMF, 40 Mol-% with regard to malyl units) was added drop-wise at RT under stirring followed by addition of 0.4 mmol of TEA. The reaction was complete after 2 h according to TLC (Rf=0 for the polymer conjugate, Rf=0.67 for LOEt; n-butanol: acetic acid:water 4:2:2) and visualization of spots by ninhydrin. Next, 0.17 mmol of TMZH (15 mg/ml in DMF, 17 Mol-% with regard to malyl units) was added drop-wise under stirring at RT followed by 0.17 mmol of TEA. After reaction completion in 2 h as judged by TLC (Rf=0.4 for TMZH; Rf=0 for the polymer conjugate; chloroform:methanol 9:1), UV and ninhydrin test, conjugate was dissolved in phosphate buffer, isolated as described for P/PEG(2%)/TMZH(30%), and freeze dried. To isolate the intermediate product P/PEG(2%)LOEt(40%), the same method for isolation was used and the product was obtained after freeze drying.

Example 7

Synthesis of Conjugate P-LLL(40%)/TMZH(17%)

PMLA activated at carboxyl groups was prepared as described for conjugate P/PEG(2%)/TMZH(30%). A solution of LLL, 0.4 mmol, 50 mg/ml in DMF (40 Mol-% with regard to malyl units) and TFA (125 Mol-% with regard to LLL, to dissolve the tripeptide) was added at RT. TEA (0.4 mmol in DMF, 1:25 v/v) was then added slowly over 30 min. After 2-3 h the reaction was complete by TLC (Rf=0 for polymer conjugate; Rf=0.6 for LLL; n-butanol:acetic acid:water 4:2:2) and by ninhydrin test. Conjugate P/LLL(40%) was dissolved in phosphate buffer and isolated as described for conjugate P/PEG(2%)/TMZH(30%). In order to maximize TMZH loading, a second round of carboxyl activation was performed: A solution of NHS (0.217 mmol) and of DCC (0.217 mmol) in 1 ml of DMF were added consecutively to the solution of 56 mg of P/LLL(40%) (0.217 mmol of free acid groups) dissolved in 1 ml of anhydrous DMF under vigorous stirring at RT. After stirring for 3 h at RT, 0.037 mmol of TMZH (15 mg/ml in DMF, 17 mol % with regard to malyl units) was added drop-wise at RT, followed by 0.037 mmol of TEA. The reaction mixture was stirred at RT for 3 h and the conjugate was isolated as described for P/PEG(2%)/TMZH(30%).

Example 8

Synthesis of P/PEG(2%)/LLL(40%)/TMZH(17%)/MEA(3%)

This conjugate was used for the conjugation of antibody. The conjugate not containing 2-MEA was synthesized in the absence of this reagent. PMLA activated at carboxyl groups was prepared as described for conjugate P/PEG(2%)/TMZH(30%). A solution of LLL, 0.4 mmol, in DMF 50 mg/ml (40 Mol-% with regard to malyl units) and TFA (125 Mol-% with regard to LLL) was added drop-wise to dissolve the tripeptide at RT. TEA 0.4 mmol in DMF (1:25 v/v) was then added slowly over 30 min. The reaction was complete after 2-3 h by TLC (Rf=0 for polymer conjugate; Rf=0.6 for LLL; n-butanol:acetic acid:water 4:2:2) and by ninhydrin test. Next, TMZH (15 mg/ml in DMF, 17 Mol-% or optionally 30 Mol-% with regard to malyl units) was added drop-wise under stirring at RT followed by equivalent amount of TEA. After reaction completion in 2-3 h, as judged by TLC (Rf=0.4 for TMZH; Rf=0 for the polymer conjugate; chloroform:methanol 9:1), UV, and ninhydrin test, 0.05 mmol of 2-MEA in DMF (100 µl, 5 Mol-% with regard to malyl units) was added to the reaction mixture. After reaction completion in 30-40 mM (TLC and ninhydrin test), conjugate was dissolved in phosphate buffer and isolated as described for conjugate P/PEG(2%)/TMZH(30%).

Example 9

Conjugate P/PEG(2%)/LLL(40%)/TMZH(17%)/HuTfR mAb(0.25%)

A solution of Anti-human TfR mAb (HuTfR)/PEG$_{3500}$/maleimide (2 mg/ml) synthesized as described (28) and dissolved in 100 mM sodium phosphate buffer containing 150 mM NaCl (pH 6.0) was added dropwise at room temperature to a solution of P/PEG(2%)/LOEt(40%)/TMZH (17%)/MEA(3%) at 2 mg/ml in the same buffer. After stirring overnight at 4° C., remaining free —SH groups were blocked by excess PDP (50 mg/ml in DMF) by stirring for 30 mM at room temperature. The product was concentrated over a centrifuge membrane filter VIVASPIN 20, cutoff 30 kDa, 20 ml at 1500×g (Sartorius Stedim Biotech, Concord, Calif., USA), and the final volume was adjusted to 2 ml before purification over SEPHADEX G-75 pre equilibrated with buffer, sodium phosphate 100 mM, NaCl 150 mM, pH 6.8. Product containing fractions were isolated, combined and concentrated via membrane filtration. Similar methods were used to synthesize other antibody containing conjugates.

Example 10

Fluorescent Labeling of Conjugates

Alex680 dissolved in DMF at 1 mg/ml was added to the solution of desired conjugates (2 mg/ml) in 100 mM sodium phosphate buffer with 150 mM NaCl, pH 5.5. The reaction mixture was stirred at RT for 1 h and passed over SEPHADEX G-75 pre equilibrated with 100 mM sodium phosphate buffer, 150 mM NaCl, pH 6.8. The product was concentrated via membrane filtration. For the antibody containing conjugates, Alex680 labeling was performed before blocking of excess free thiol groups by PDP.

Example 11

Calculation of Molecular Weights of Nanoconjugates

Molecular weights of nanoconjugates were calculated as shown for conjugate P/PEG(2%)/LLL(40%)/TMZH(17%) as an example: 100% malic acid residues (FW 116)=862 monomers of PMLA (Mw=100 kDa). Mw fraction of malic acid with free —COOH (FW116) is 41%=353.4×116 Da: 41.0 kDa. Fraction conjugated malic acid (FW 99) is 59%=508.6×99 Da: 50.3 kDa. Fraction mPEG$_{5000}$ (FW 5000) is 2%=17.2×5000 Da: 86.2 kDa. Fraction LLL (FW 357.5) is 40%=344.8×357.5 Da: 123.3 kDa. Fraction TMZH (FW 210.63) is 17%=146.5×210.63: 30.8 kDa. Total estimated average Mw of conjugate is 332 kDa.

Example 12

Hydrodynamic Diameter and Zeta Potential

Synthesized conjugates were characterized with respect to their size and ζ potential using a particle and molecular size analyzer ZETASIZER Nano ZS90 (Malvern Instruments, Malvern, UK). The size was calculated on the basis of noninvasive back-scattering (NIBS) measurements using the Stokes-Einstein equation, $d(H)=kT/3\pi\eta D$. $d(H)$ is the hydrodynamic diameter, D translational diffusion coefficient, k Boltzmann's constant, T absolute temperature, and, viscosity. The diameter that is measured in DLS (Dynamic Light Scattering) refers to the particle diffusion within a fluid and is referred to as the hydrodynamic diameter corresponding to the diameter of a sphere that has the same translational diffusion coefficient as the particle. The $\zeta$ potential was calculated from the electrophoretic mobility based on the Helmholtz-Smoluchowski formula, using electrophoresis M3-PALS (29, 30). All calculations were carried out by the ZETASIZER 6.0 software. For the particle size measurements at 25° C., the solutions were prepared in PBS at a concentration of 2 mg/ml, filtered through a 0.2 μm pore membrane. For the measurement of the $\zeta$ potential, the concentration of the sample dissolved in water containing 10 mM NaCl was 2 mg/ml, and the voltage applied was 150 V. All the conjugate solutions were prepared immediately before analysis at 25° C. Data represent the mean±standard deviation obtained for three measurements.

Example 13

Liposome Leakage Assay

Fluorescent assay for calcein release from loaded phosphatidylcholine/cholesterol liposomes (31) purified over the SEPHADEX G-50 gel was used to determine leakage activity of synthesized polymer conjugates. To assess leakage at different pH values, nanoconjugates were serially diluted in 50 μl buffer containing appropriate mixtures of 137 mM HEPES, pH 7.4 and 137 mM citrate, pH 5.0. Triplicate samples were mixed with 50 μl liposome suspensions in 5 mM HEPES buffer, 150 mM NaCl, pH 7.4 (final lipid concentration 160 μM). After 1 h at RT, fluorescence was read by an ELISA reader at 485 nm excitation and 535 nm emission wavelengths. The detergent TRITON X-100, 0.25% (v/v), was used as a reference for 100% leakage.

Example 14

Conjugate Degradation Study

The degradation of nanoconjugates in human plasma was carried out at 37° C. with a polymer concentration of 1 mg/ml. The sample vials were sealed to avoid evaporation and stored at 37° C. in an incubator. For the isolation from the plasma, aliquots of 1 ml were extracted with 5 ml of chloroform/ethyl acetate (1:1 v/v). The copolyester contained in the organic phase was dried and re-dissolved in PBS buffer. Size reduction due to degradation was followed by measurement of the hydrodynamic diameter in a particle and molecular size analyzer ZETASIZER or of the molecular weight by SEC-HPLC. Sample preparation with the polymers of known Mw was used to verify that the isolation method had no effect on molecular weights. Degradation in PBS (pH 7.4) was followed at a concentration of 1 mg/ml for each copolymer. The change in size of the nanoconjugate either by SEC-HPLC or hydrodynamic diameter (a particle and molecular size analyzer ZETASIZER) was measured as a function of degradation time. Molecular weights $M_w(t)$ and hydrodynamic diameter (t) were plotted as a function of degradation time with reference of these properties at zero incubation time.

Example 15

Cell Viability

Primary glioma cell lines U87MG and T98G, and invasive breast carcinoma cell lines MDA-MB-231 and MDA-MB-468 were obtained from American Type Culture Collection (ATCC, Manassas, Va., USA) USA. U87MG and T98G cells were cultured in MEM supplemented with 10% fetal bovine serum, 1% MEM NEAA, 1 mM sodium pyruvate and 2 mM L-glutamine. For MDA-MB-231 and MDA-MB-468, Leibovitz's L-15 medium with 10% fetal bovine serum was used. Cells were seeded at $10^3$ per well (0.1 ml) in 96-well flat-bottomed plates and incubated overnight at 37° C. in humid atmosphere with 5% $CO_2$ (MDA-MB-231 and MDA-MB-468 were incubated without $CO_2$). After exposure to synthesized conjugates for 24 h, medium was replaced every 48 h. Cell viability was measured on day 5 for T98G and day 7 for the rest of the cell lines using the CELLTITER 96 Aqueous One Solution Cell Proliferation Assay kit (Cat. No. PR-G3580; Promega, Madison, Wis., USA). Yellow [3-(4,5-dimethylthiazol-2-yl)-5-(3-carboxymethoxyphenyl)-2-(4-sulfophenyl-)-2H-tetrazolium, inner salt] (MTS) is bioreduced by cells into formazan that is soluble in the tissue culture medium. The absorbance reading at 490 nm from the 96-well plates is directly proportional to the number of living cells (32). The viability of the untreated cells was taken as 100%. The results shown are the means±standard deviation of three independent measurements. Data were analyzed by statistical software GRAPHPAD PRISM 3.0.

Example 16

Confocal Microscopy $1\times10^5$ U87MG cells were seeded on Lab-Tek chamber slides (Thermo Fisher Scientific, Rochester, N.Y., USA) for 24 h. The cells were washed once with serum-free media and incubated with Alex680 fluorescently labeled conjugates in 500 μl serum-free media at 50 μg/ml for P/PEG(2%)/LLL(40%)TMZH(17%)/Alex680(1%) and at 100 μg/ml for P/PEG(2%)/LLL(40%)TMZH(17%)/HuTfR mAb(0.25%)/Alex680(1%). After 1 h incubation at 37° C. in humid atmosphere with 5% $CO_2$, the cells were washed three times with PBS and finally incubated in fresh media with serum for live confocal imaging in a TCS SP spectral scanner (Leica Microsystems, Mannheim, Germany) Image stacks of 246 by 246 μm in size and 7.5 μm in depth of live U87MG glioma cells were acquired with a HCX PL APO CS 63.0×1.20 lens. Live cells were placed on chamber slides maintaining 37° C. temperature, humidity and 5% $CO_2$ by a separate lens and chamber heating system. The spectral settings were optimized for Alex680, excitation 670 nm and emission 685-750 nm. The images were processed by ImageJ 1.410 software from NIH.

Example 17

Nanoconjugate Syntheses

The multi component drug delivery system schematically presented in FIG. 1 was synthesized with PMLA as the platform and prodrug TMZ in its hydrazide form, $H_2$N-Leu-Leu-LeuOH (LLL) or $NH_2$-LeuOEt (LOEt) for disruption of endosomal membrane, antibodies for targeting, and PEG against resorption and enzyme degradation. The first part of the conjugation included the chemical activation of the PMLA pendant carboxyl groups forming the NHS-ester and subsequently the nucleophilic replacement by forming stable amide bonds. Conjugation of antibodies via thioether bond formation followed in the second part. Because of the PMLA chain length inhomogeneity, an excess of mAb was chosen in order to increase the likelihood that at least one molecule was conjugated with each polymer chain. The amount of 40% of carboxyl groups conjugated with LLL for most efficient membrane disruption activity limited the amount of TMZH conjugation to 17%. In order to increase the amount of TMZH loading, carboxyl activation was repeated after conjugation with LLL before conjugation with TMZH. Obtained nanoconjugates of higher than 17% TMZH were, however, found insoluble in aqueous buffer. Care was taken to avoid neutral or alkaline conditions as well as elevated temperatures (>22° C.) in order to keep hydrolytic degradation of TMZ at a minimum. Freeze-dried intermediates and products could be stored at −20° C. for several months without measurable loss in chemical or physiological reactivity.

Example 18

Purity and Physicochemical Characterization

Figure 2:
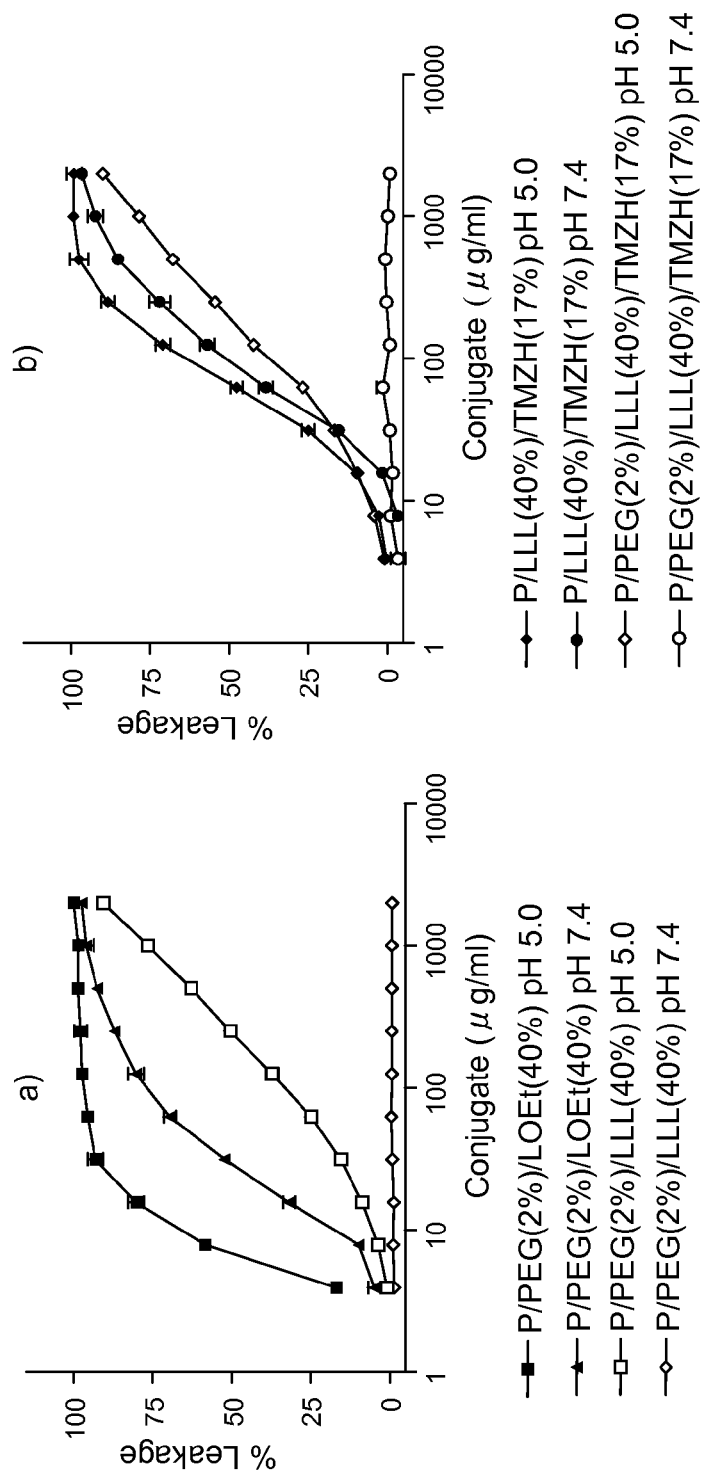
FIG. 2 depicts, in accordance with an embodiment herein, liposomal leakage assay: a) Liposome leakage of P/LOEt and P/LLL conjugates, b) Liposome leakage of P/LLL/TMZH and P/PEG/LLL/TMZH conjugates. Percentage refers to ratio of pendant —COOH conjugated (total PMLA pendant —COOH is 100%). % Leakage compared to complete leakage in the presence of the detergent TRITON X-100 0.25% (v/v).
Figure 6:
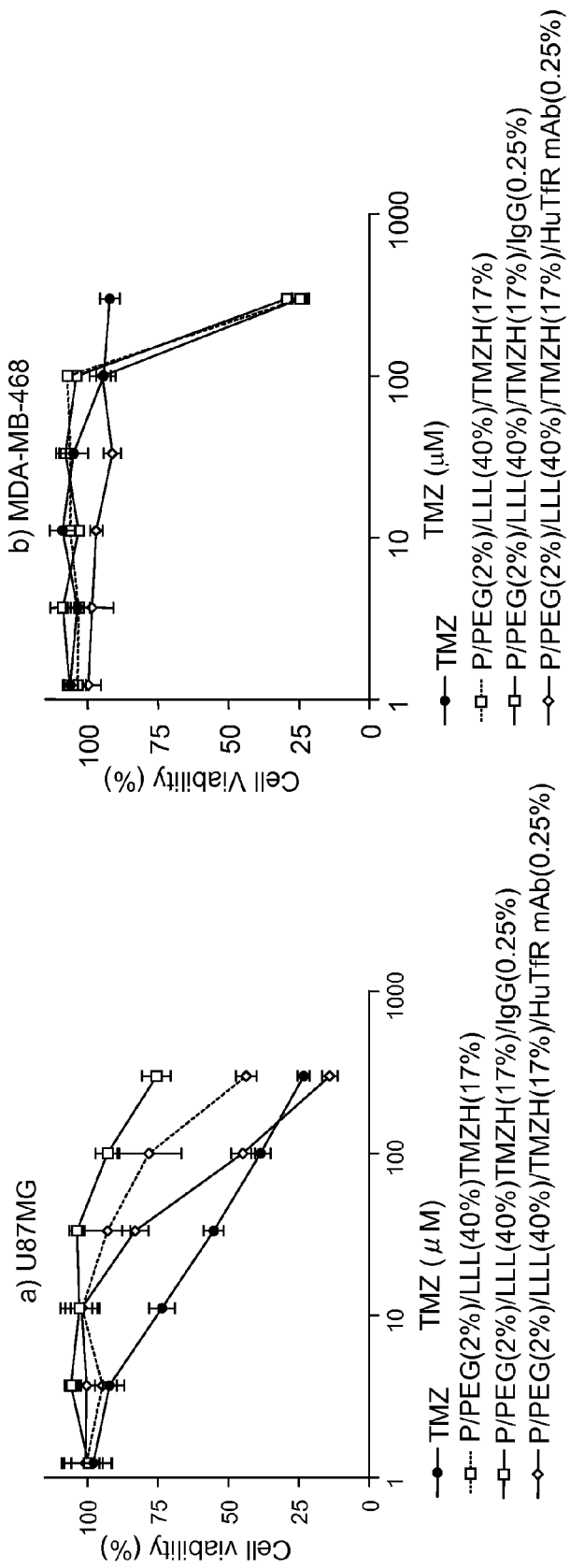
FIG. 6 depicts, in accordance with an embodiment herein, cell viability of LLL nanoconjugates with antibody: Effects on cell viability of TMZ, P/PEG(2%)/LLL(40%)/TMZH (17%), P/PEG(2%)/LLL(40%)/TMZH(17%)/IgG(0.25%), P/PEG(2%)/LLL(40%)/TMZH(17%)/HuTfR mAb(0.25%) on a) U87MG and b) MDA-MB 468 cells. Conjugation of HuTfR mAb increased the activity of drug on U87MG cell line, whereas no such effect was observed on MDA-MB-468.

Products were highly soluble in aqueous solution without forming precipitates as judged by SEC-HPLC and a particle and molecular size analyzer ZETASIZER. Preparations were tested for small molecular weight impurities by TLC and ninhydrin reaction. On this basis of SEC-HPLC results (using multiple wavelengths for scanning) and hydrodynamic diameter scanning, the investigated conjugates were pure, i.e. consisting of single compounds. The amount of TMZH in the conjugate preparations was validated by UV absorbance at 328 nm using known amounts of free TMZH as standards. By $^1$H NMR analysis using integration of methyl group signals of TMZH and of PMLA protons the TMZH contents were analyzed. TMZ contents by NMR and UV measurement were the same within 3% deviation measured for conjugate P/PEG(2%)/TMZH(30%). Conjugates had characteristic values of hydrodynamic diameters and zeta potentials (Table I). Free PMLA and P/LLL(40%)/TMZH(17%) had the smallest hydrodynamic diameter, whereas additionally conjugated PEG$_{5000}$ increased the diameter by about 2 nm and mAb, by about 8 nm. The value of ζ potential can be used to differentiate between PMLA, −22.9 mV, and nanoconjugates with neutral ligands like TMZH, LOEt, for example −7 mV for P/PEG(2%)/LOEt (40%)/TMZH(17%), and conjugates with charged ligands like LLL (instead of LOEt), for example −11.5 mV for P/PEG(2%)/LLL(40%)/TMZH(17%) (Table 1). Conjugates were also distinguished by other properties, e.g., by their capability for liposome leakage. As shown in FIG. 2, the conjugate P/PEG(2%)LLL(40%)/TMZH(17%) was pH-sensitive, whereas the conjugate P/LLL(40%)/TMZH(17%) was not. Another property was the effect on U87MG and MDA-MB-468 cell viability. It was more affected by the conjugate P/LLL(40%)/TMZH(17%) (FIG. 4) than by P/PEG(2%)LLL(40%)/TMZH(17%) (FIG. 6).

Example 19

Half-Life of Free and Conjugated TMZH

TMZ is a prodrug and undergoes spontaneous conversion to the active alkylating agent at neutral or alkaline pH. Half-lives were measured at physiological pH 7.4 in PBS and summarized in Table I. The decomposition of free and conjugated TMZH by hydrolytic ring opening (Chart 1) was a first order reaction for free TMZ or TMZH and conjugated TMZH (data not shown). For TMZ, the half-life was 1.80±0.1 h and for TMZH, 1.98±0.1 h. Half-life was significantly enhanced, about 3-4 times, after conjugation with the polymer. For example, TMZ had a half life of 7.34±0.2 h for conjugate P/LLL(40%)/TMZH(17%) and 7.10±0.2 h for P/PEG(2%)/TMZH(30%) (Table I). Similar data have been reported for TMZ conjugated with small carbon chains (6). No detectable decomposition was observed during 24 h at pH 5.0 at RT.

Example 20

Stability and Degradation Measured by Size

Figure 3:
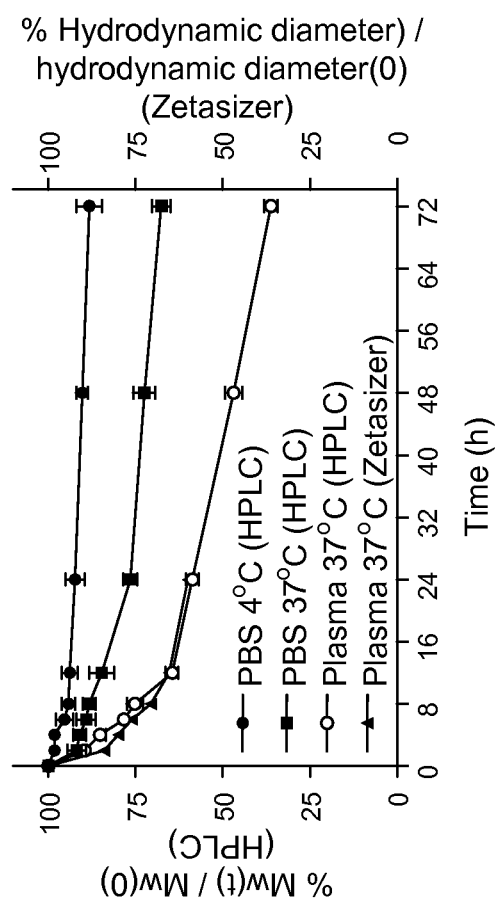
FIG. 3 depicts, in accordance with an embodiment herein, nanoconjugate degradation in PBS and human plasma. Degradation of conjugate P/LLL(40%)TMZH(17%) in PBS and human plasma at 4° C. and 37° C. studied by relative changes in molecular size indicated by column retention times (% molecular weights) of SEC-HPLC and hydrodynamic diameter measured by a particle and molecular size analyzer ZETASIZER. 100% refers to the size at time zero.

Degradation of synthesized nanoconjugates was measured by SEC-HPLC and a particle and molecular size analyzer ZETASIZER in terms of molecular weight and hydrodynamic diameter respectively (data not shown). In PBS at 4° C., all synthesized nanoconjugates were stable maintaining over 85% of original $M_w$/size for more than 72 h. However, at temperatures 25° C. and especially at 37° C., substantial degradation was observed and $M_w$/size was reduced to 50% after 24-72 h in PBS. In human plasma at 37° C., conjugates degraded more rapidly compared with degradation in PBS and $M_w$/size was reduced by 50% after 12-36 h. As an example, degradation of conjugate P-LLL (40%)/TMZH(17%) is shown in FIG. 3.

Example 21

Membrane Destabilization

As an uncharged prodrug, TMZ can passively permeate the cells, where it is ultimately activated to the nucleic acid methylating methyldiazonium cation (33). Targeting of glioma cells by conjugated mAb would involve binding of the nanoconjugate delivery vehicle to overexpressed TfR and subsequent internalization into the endosomal system. In order to deliver the desired drug into the cytoplasm, disruption of the endosomal membrane would be essential. By systematic structure variation using PMLA as nanoplatform and membranes of artificial liposomes we have found LOEt and LLL substituting 40% of pendant PMLA carboxylates of the platform to be excellent candidates for endosomal membrane disruption (FIG. 2). Whereas the LLL unit was active only at pH 6-5.0 (FIG. 2a), resembling pH of late endosomes and lysosomes, the membrane disruption activity of the LOEt unit was pH-independent. The pH-dependence for LLL was referred to the ionization of the tripeptide carboxyl group. The $pK_a$ that governs ionization was shifted by conjugation with PMLA towards the neutral pH region due to the hydrophobic shielding by the multiple conjugated leucine side chains (Ding et al. "Poly(β-L-malic acid) with pendent leu-leu-leu-OH for endosome-routed cytoplasmic delivery". 14th International Symposium on Recent Advances in Drug Delivery Systems, Salt Lake City, 2009, Abstract #91). FIG. 2 shows examples of liposome leakage caused by membrane disruption in the absence and presence of TMZH. LOEt was the more effective membrane disrupting agent (FIG. 2a). The loading by TMZH slightly increased the liposome leakage activity by LOEt and LLL units, but did not abolish the pH dependence for conjugate P/PEG(2%)LLL(40%)/TMZH(17%) (FIG. 2b). When TMZH was conjugated as in P/LLL(40%)/TMZH(17%), the leakage activity was improved and the pH-sensitivity disappeared (FIG. 2b). Most likely, this change was attributed to conjugation of TMZH with LLL-COOH residues thus eliminating the carboxylates that before gave rise to the observed pH dependence.

Example 22

Cell Viability Study

Figure 4:
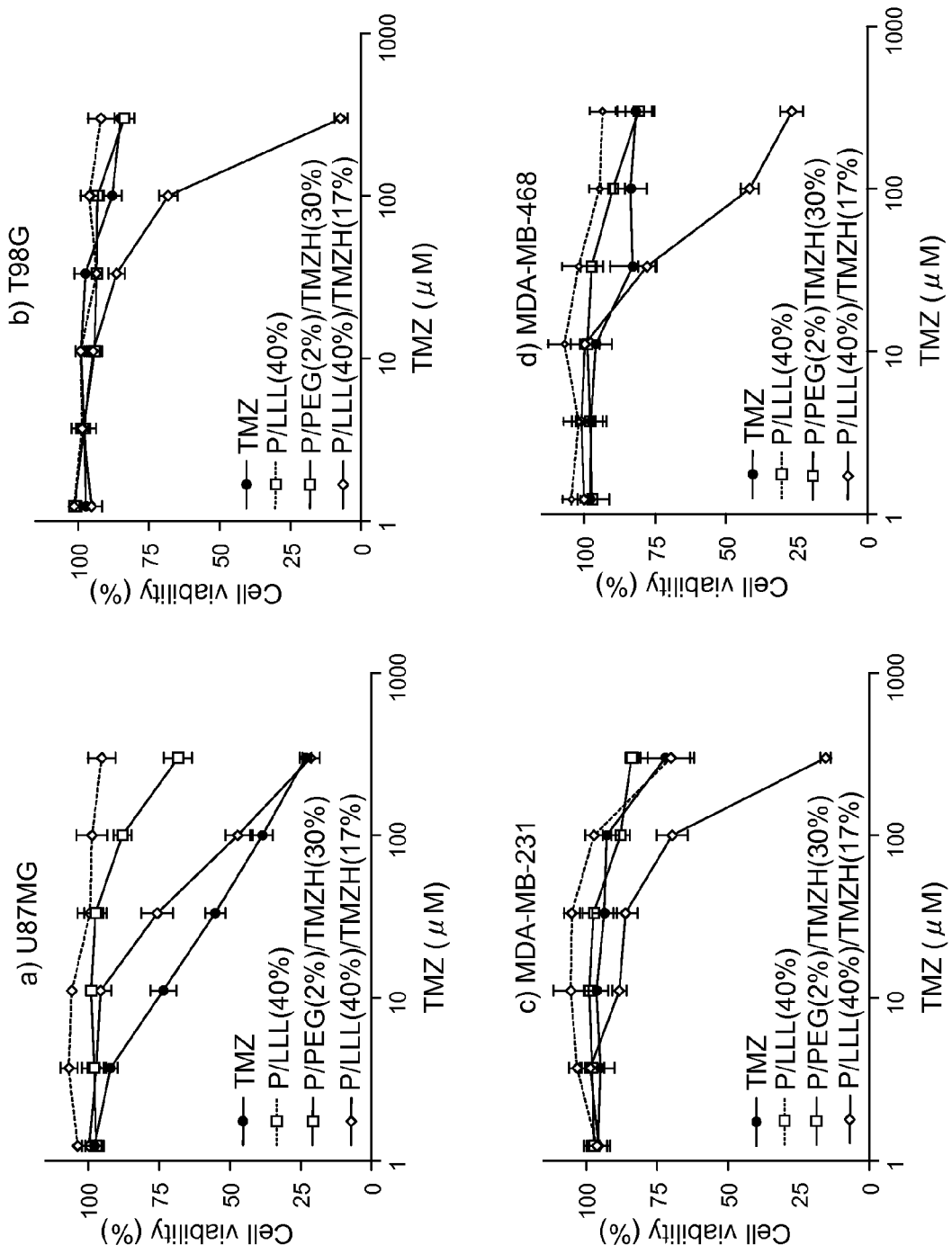
FIG. 4 depicts, in accordance with an embodiment herein, cell viability of nanoconjugate with LLL: Effects on cell viability of TMZ, P/LLL(40%), P/PEG(2%)/TMZH(30%) and P/LLL(40%)/TMZH(17%) on a) U87MG, b) T98G, c) MDA-MB-231 and d) MDA-MB-468 cells. Nanoconjugate P/LLL(40%) without drug was used as a control for the conjugate P/LLL(40%)/TMZH(17%) with drug and contains equivalent amount of polymer backbone. Nanoconjugate P/PEG(2%)/TMZH(30%) even with high loading of TMZH but without LLL endosome escape unit was only marginally effective. P/LLL(40%)/TMZH(17%) was the most effective nanoconjugate.
Figure 5:
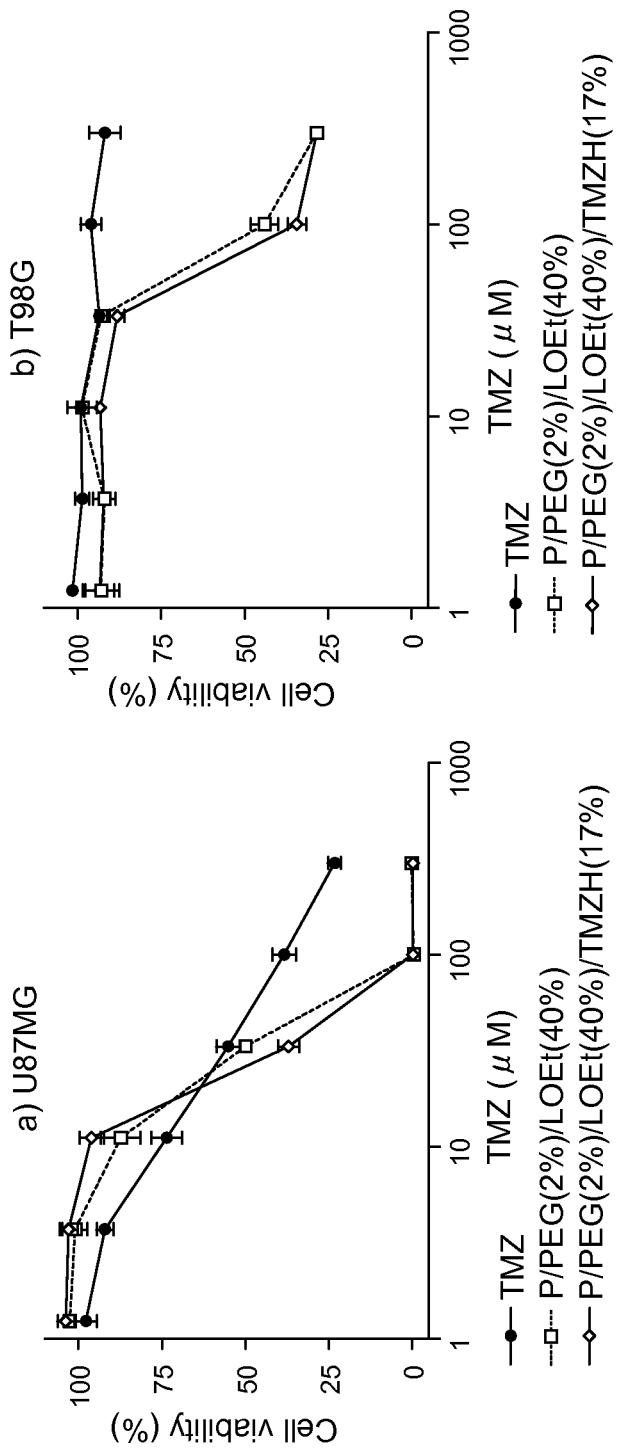
FIG. 5 depicts, in accordance with an embodiment herein, cell viability of nanoconjugate with LOEt: Effects on cell viability of TMZ, P/PEG(2%)/LOEt(40%) and P/PEG(2%)/LOEt(40%)/TMZH(17%) on a) U87MG and b) T98G cells. Nanoconjugate P/PEG(2%)/LOEt(40%) without drug was used as a control for the conjugate P/PEG(2%)/LOEt(40%)/TMZH(17%) with drug and contains equivalent amount of polymer backbone.

Effects of the nanoconjugates on cell viability were measured in order to investigate the influence of the delivery system on the TMZH prodrug activity and to test for cytotoxic activities of the delivery system itself in the absence of the prodrug. Results were compared with those for free TMZ and TMZH in a dose-dependent manner. P/PEG(2%)/TMZH(30%) had no significant effect on viability compared with free TMZ in the case of human glioma cell line U87MG (FIG. 4a), and it was ineffective on T98G, MDA-MB-231 and MDA-MB-468 cell lines (FIG. 4b-d). Conjugation of membrane disruption unit had pronounced effects on cell viability. Introduction of LOEt as a membrane disruption unit seemed to decrease cell viability significantly (FIG. 5); however, the decrease was apparently due to the nanoconjugate P/PEG(2%)/LOEt(40%) carrier itself and not by conjugated TMZH. As LOEt negatively affected cell viability in the observed concentration range, conjugates with this endosomal escape unit were not further considered. Importantly, introduction of LLL in the conjugate P/LLL (40%)/TMZH(17%) significantly decreased cell viability of all four cell cultures, gliomas U87MG and T98G, and breast cancer cell lines MDA-MB-231 and MDA-MB-468. In the same assay, free TMZ was inactive in all lines except U87MG. Conjugate P/LLL(40%) as a control had little or no effect on cell viability due to the absence of the prodrug (FIG. 4) and this was not changed by the addition of $PEG_{5000}$. The effect of coupling anti-TfR mAb to the nanoconjugate is shown in FIG. 6a. Whereas free TMZ had a stronger effect on U87MG cells than the nanoconjugates, these showed an increasing potency in the order P/PEG (2%)/LLL(40%)/TMZH(17%)/IgG(0.25%)<P/PEG(2%)/ LLL(40%)/TMZH(17%)<P/PEG(2%)/LLL(40%)/TMZH (17%)/HuTfR mAb(0.25%)<TMZ. In contrast, with the cell line MDA-MB-468, free TMZ was ineffective at all concentrations below 130 µM, whereas conjugates P/PEG(2%)/ LLL(40%)/TMZH(17%)/IgG(0.25%), P/PEG(2%)/LLL (40%)/TMZH(17%), P/PEG(2%)/LLL(40%)/TMZH(17%)/ HuTfR mAb(0.25%) showed significant reduction in viability and were almost equally effective.

Example 23

Confocal Microscopy

Figure 7:
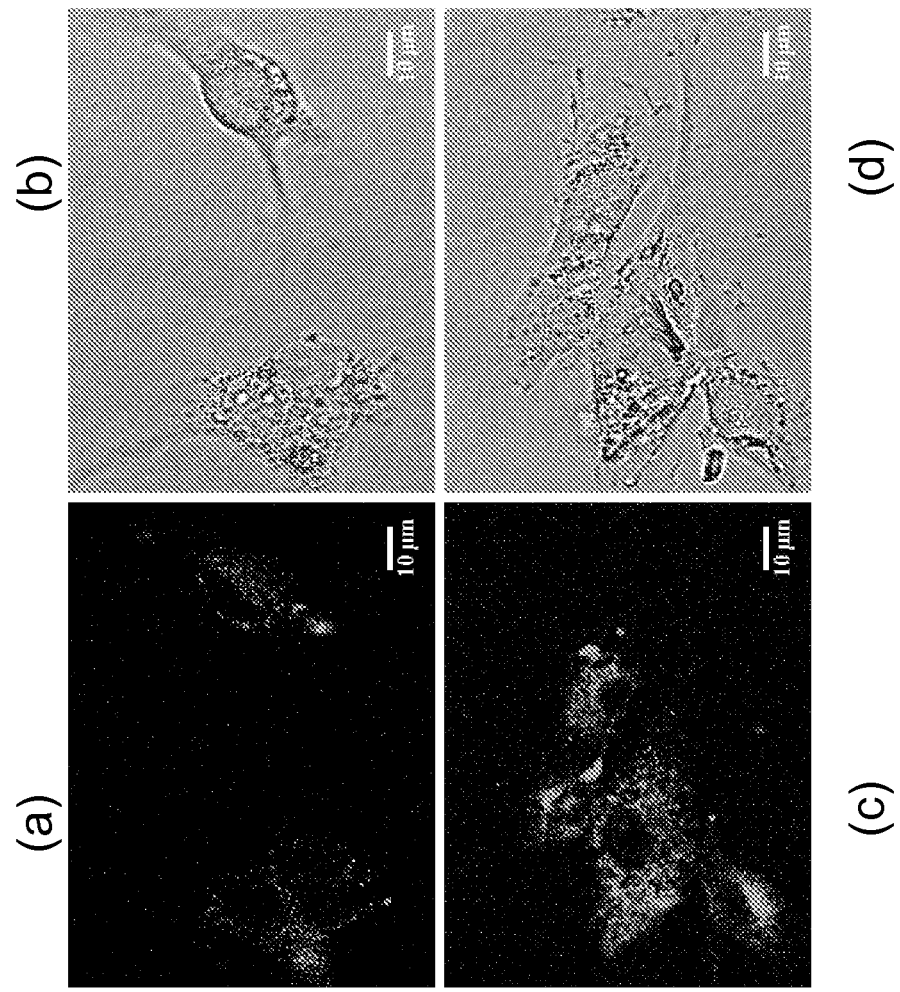
FIG. 7 depicts, in accordance with an embodiment herein, drug internalization into cultured human glioma U87MG cells by confocal microscopy: a) 1 h incubation with fluorescently labeled conjugate P/PEG(2%)/LLL(40%)TMZH (17%)/Alx680(1%). The location of conjugate is indicated by fluorescence; b) phase contrast; c) 1 h incubation with fluorescently labeled conjugate P/PEG(2%)/LLL(40%) TMZH(17%)/HuTfR mAb(0.25%)/Alx680(1%). The location of conjugate is indicated by fluorescence; d) phase contrast.
Figure 8:
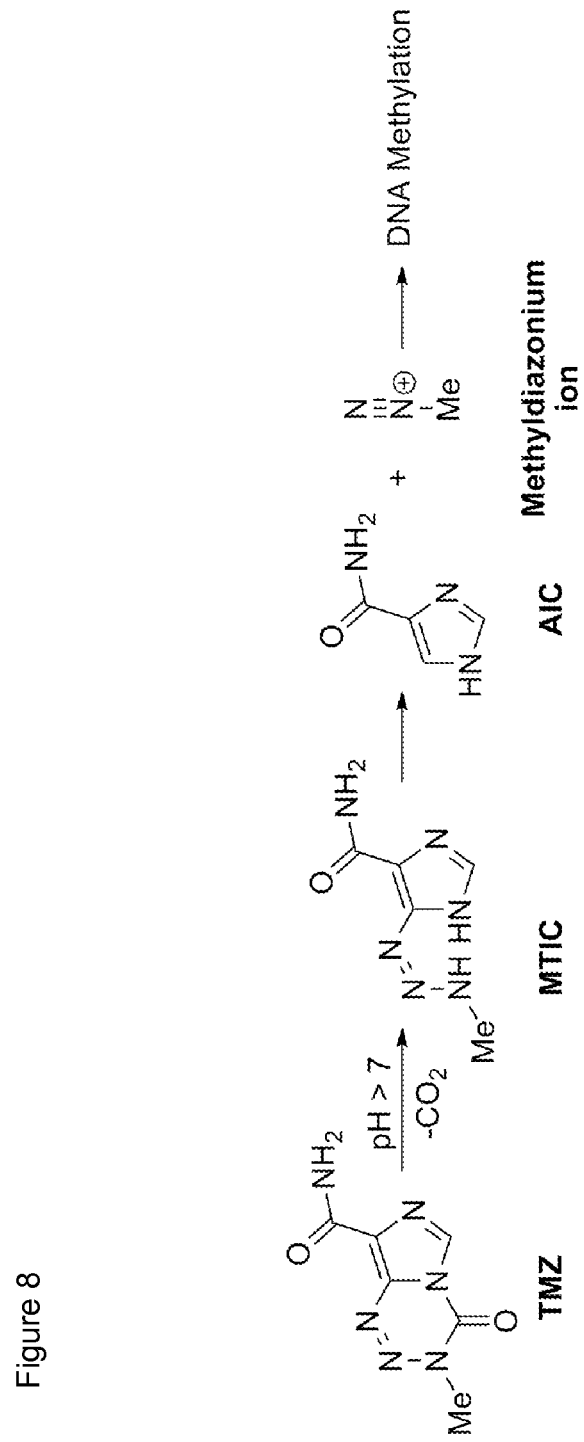
FIG. 8 depicts, in accordance with an embodiment herein, pH-dependent conversion of TMZ to metabolites, 5-(3-methyltriazen-1-yl)imidazole-4-carboxamide (MTIC), 4-amino-5-imidazole-carboxamide (AIC), methyldiazonium ion and DNA methylation (6).
Figure 9:
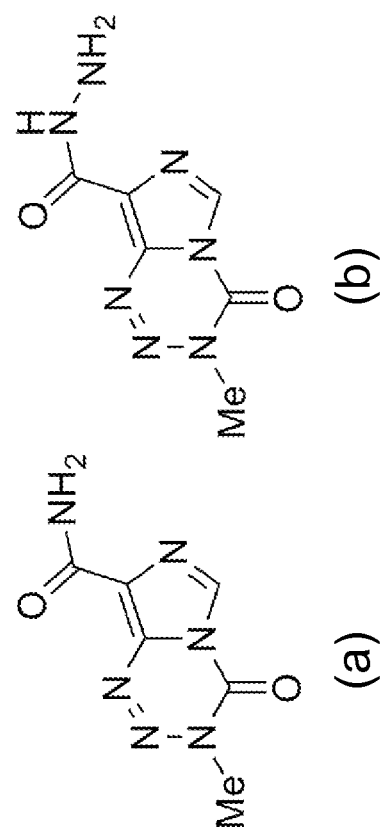
FIG. 9 depicts, in accordance with an embodiment herein, (a) temozolomide (TMZ) and (b) temozolomide hydrazide (TMZH).

The uptake of nanoconjugates was imaged by confocal microscopy following the appearance of fluorescence inside live human glioma U87MG cells (FIG. 7). Uptake into vesicles was observed for both conjugates P/PEG(2%)/LLL (40%)/TMZH(17%) and P/PEG(2%)/LLL(40%)/TMZH (17%)/HuTfR mAb(0.25%) labeled with Alex680. At a fixed instrument setting, the intensity and the number of vesicles was higher for the actively targeting conjugate with TfR mAb than for the conjugate lacking the antibody. It can be concluded that the nanodrugs were internalized most likely by receptor-mediated endocytosis and possibly also by pinocytotic pathways.

Example 24

Discussion

Orally applied TMZ to treat human gliomas has the potency to be distributed all over the entire organism. After penetration of the lipophilic prodrug through membranes into the cytoplasm of recipient cells it will be activated by the hydrolytic mechanism described herein. The active drug is then ready to methylate proteins and especially DNA, guanine at N7 position, followed by methylation of adenine at the O3 position and of guanine at the O6 position (33). Failure of repair will drive these cells into apoptosis. Hydrolytic activation of the prodrug at sites other than the cytoplasm is inefficient due to the fact that the cationic methyl diazonium like any other charged molecule cannot passively penetrate membranes.

The inventors have succeeded to conjugate TMZ via the hydrazide bond to the highly negatively charged PMLA that renders the prodrug no longer diffusible through membranes. As a consequence, the active methyl diazonium cation can only be generated from the nanodrug. Free passive diffusion of the PMLA conjugate into recipient cells is highly unlikely because of its high negative charge, and generation of active drug outside the cytoplasm would not be effective due to its own intrinsic charge. Therefore, the nanodrug can only give rise to nucleic acid methylation if it is internalized into the cytoplasm of recipient cells. The results in FIG. 7 show that drug uptake follows most likely receptor-mediated endocytosis and possibly pinocytotic pathways of the conjugates P/PEG(2%)/LLL(40%)/TMZH (17%)/HuTfR mAb(0.25%) and P/PEG(2%)/LLL(40%)/ TMZH(17%) that were labeled with Alex680. Without exiting from the endosome into the cytoplasm, drug activation would be still ineffective due to the vesicle membrane barrier, explaining why conjugate P/PEG(2%)/TMZH(30%) without any endosome disruption unit did not affect cell viability (FIG. 4). Moreover, maturing endosomes undergo acidification rendering drug activation unlikely, because this requires neutral or higher pH. If the nanodrug carries the membrane disrupting LLL device as in the case of the above conjugates, it could enter the cytoplasm, and there, by virtue of physiological pH, the prodrug could be converted into its active form and methylate DNA.

To satisfy the above mechanism, the inventors synthesized the nanodrug carrying targeting TfR antibodies, endosome escape unit, and the prodrug. The results in FIGS. 4 and 6 show the delivery and prodrug activation to follow the anticipated mechanism. The effect of the targeting HuTfR mAb was observed in the case of human glioma U87MG cells. A significant reduction of viability is seen in the presence of the endosome escape unit LLL for all cell lines shown in FIGS. 4 and 6. This in agreement with the stringent requirement for endosome escape in the prodrug delivery mechanism.

Whereas glioma U87MG cells responded to treatment with free TMZ, cell viability of glioma T98G and breast cancer MDA-MB-231 and MDA-MB-468 cells did not change. These cell lines are known to be TMZ resistant (32-34). In the case of T98G cells, resistance has been referred to overproduction of O6-methyl guanine methyltransferase (MGMT) (32), that of MDA-MB-231 cells has been associated with unbalanced expression of DNA glycosylase and DNA polymerase expression (34), and the mechanism of resistance is not known for MDA-MB-468 cells. If indeed the lack of response to free TMZ for T98G, MDA-MB-231 and MDA-MB-468 in FIG. 4 referred to TMZ resistance, the observed significant decrease of cell viability (FIGS. 4 and 6) showed that the nanoconjugates P/PEG(2%)/LLL(40%)/TMZH(17%), P/LLL(40%)/TMZH (17%)/HuTfR mAb (0.25%) and P/LLL(40%)/TMZH (17%)/IgG(0.25%) had the ability to overcome the resistance. On the basis of their unique results, conjugates P/PEG(2%)/LLL(40%)/TMZH(17%) and P/LLL(40%)/TMZH(17%)/HuTfR mAb(0.25%) were designed as lead compounds with potential for treatment of glial tumors in vivo.

The drug delivery system offers a biodegradable, non-toxic, and non-immunogenic scaffold obtained from a biological source, thus opening an avenue for drug delivery without the danger of liver storage disease. Conjugation of TMZH to this platform has been challenging because of the sensitivity of the prodrug to neutral and alkaline pH. Nonetheless, syntheses of TMZ nanodrugs have been worked out to be readily achievable and highly reproducible. The solution properties such as solubility and absence of aggregation, size in the nanometer range, and slightly negative zeta potential are favorable for drug delivery (35, 36). One of the lead conjugates contains $PEG_{5000}$, which minimizes enzymatic nanodrug degradation and clearance by the reticuloendothelial system (37). The nanodrugs are stable in human plasma over several hours, and the range of half-life for active drug formation has increased several-fold over that of free TMZ by conjugation to the PMLA platform. The increased half-life of conjugated TMZ favors an efficient delivery of functional prodrug in vivo. On the basis of the data, the following in vivo scenario is likely: After I.V. application, the nanodrug will be accumulated in the interstitial space of malignant glioma by EPR effect (19) and/or active mAb targeting of overexpressed TfR on vascular endothelium next to the tumor (21). From the interstitium, the nanodrug will enter the endosomal system of tumor cells and become activated in the cytoplasm after endosomal escape. Accumulation in the tumor by EPR effect and especially, active mAb targeting provides efficiency of tumor treatment with minimal side effects for healthy tissue.

Example 25

TABLE 1

Physicochemical properties of the conjugates and half-lives of TMZ

| Conjugates | Hydrodynamic diameter (nm)$^a$ | Zeta potential (mV)$^b$ | Half-life of TMZ (h)$^c$ |
|---|---|---|---|
| TMZ | n.d. | n.d. | 1.80 (±0.1)$^d$ |
| TMZH | n.d. | n.d. | 1.98 (±0.1) |
| PMLA | 6.6 (±0.1) | 22.9 (±1.7) | n.d. |
| P/PEG(2%)/TMZH(30%)$^e$ | 7.8 (±0.4) | 16.1 (±1.2) | 7.10 (±0.2) |
| P/PEG(2%)/LOEt(40%)/TMZH(17%) | 8.5 (±0.4) | −6.7 (±0.2) | 4.92 (±0.3) |
| P/PEG(2%)/LLL(40%)/TMZH(17%) | 6.9 (±1.3) | 11.5 (±1.8) | 6.25 (±0.2) |
| P/LLL(40%)/TMZH(17%) | 6.5 (±0.2) | 17.7 (±2.1) | 7.34 (±0.2) |
| P/PEG(2%)/LLL(40%)/TMZH(17%)/HuTfR mAb(0.25%) | 14.8 (±2.1) | −6.3 (±1.7) | n.d. |

$^a$Hydrodynamic diameter at 25° C. measured in PBS at a concentration of 2 mg/ml;
$^b$ζ potential at 25° C. in aqueous solution of 10 mM NaCl at 150 V;
$^c$half-life measured at physiological pH in PBS at 37° C.;
$^d$Mean values and S.D. for three independent measurements;
$^e$percentage refers to total number (100%) of pendant carboxyl groups in unsubstituted PMLA;
n.d., not done.

Example 26

Conclusions

For the purpose of targeting TMZ to human glioma, TMZH was conjugated to PMLA platform, which was equipped with anti-human TfR antibodies for tumor cell targeting by receptor mediated endocytosis; and pH-dependent LLL for endosome escape. The lead compounds P/PEG (2%)/LLL(40%)/TMZH(17%)/HuTfR mAb(0.25%) and P/LLL(40%)/TMZH(17%) showed significant reduction in tumor cell viability of both human glioma and human breast cancer cell lines. Cell viability was significantly reduced in cases of TMZ-resistant cell lines where free TMZ had no effect.

Example 27

Efficacy of Delivery System In Vivo

After numerous in vitro screening, it was important to investigate the efficacy of delivery system in vivo. To prove the concept, subcutaneous model was used using human glioma U87MG cell line. $3 \times 10^6$ cells were inoculated in nude mice and tumors were formed. Conjugate P/PEG(2%)/ LLL(40%)/TMZ(15%) was chosen for the in vivo study and was synthesized following a similar procedure described for conjugate P/PEG(2%)/LOEt(40%)/TMZH(17%).

After inoculation of human glioma cells in nude mice, all the animals were randomized as the average tumor volume reached about 125 mm$^3$ (day 28 after inoculation). Animals were divided in two different groups as shown in Table 2. Nanoconjugates are highly soluble in aqueous solutions and were dissolved in PBS prior to the administration. Drug was administered intravenously (I.V.) for five consecutive days at a temozolomide concentration of 4 mg/kg. Tumor volume was measured 3 times a week and all the animals were euthanatized on day 37.

TABLE 2

Treatment plan for tumor bearing mice with temozolomide nanoconjugate.

| Group 1 | Group 2 |
|---|---|
| n = 4 | n = 4 |
| PBS | P-PEG(2%)LLL(40%)/TMZ (15%) |
| IV for 5 days for 5 days | 4 mg/kg (TMZ concentration) 65 mg/kg (nanoconjugate concentration) IV for 5 days |

Figure 12:
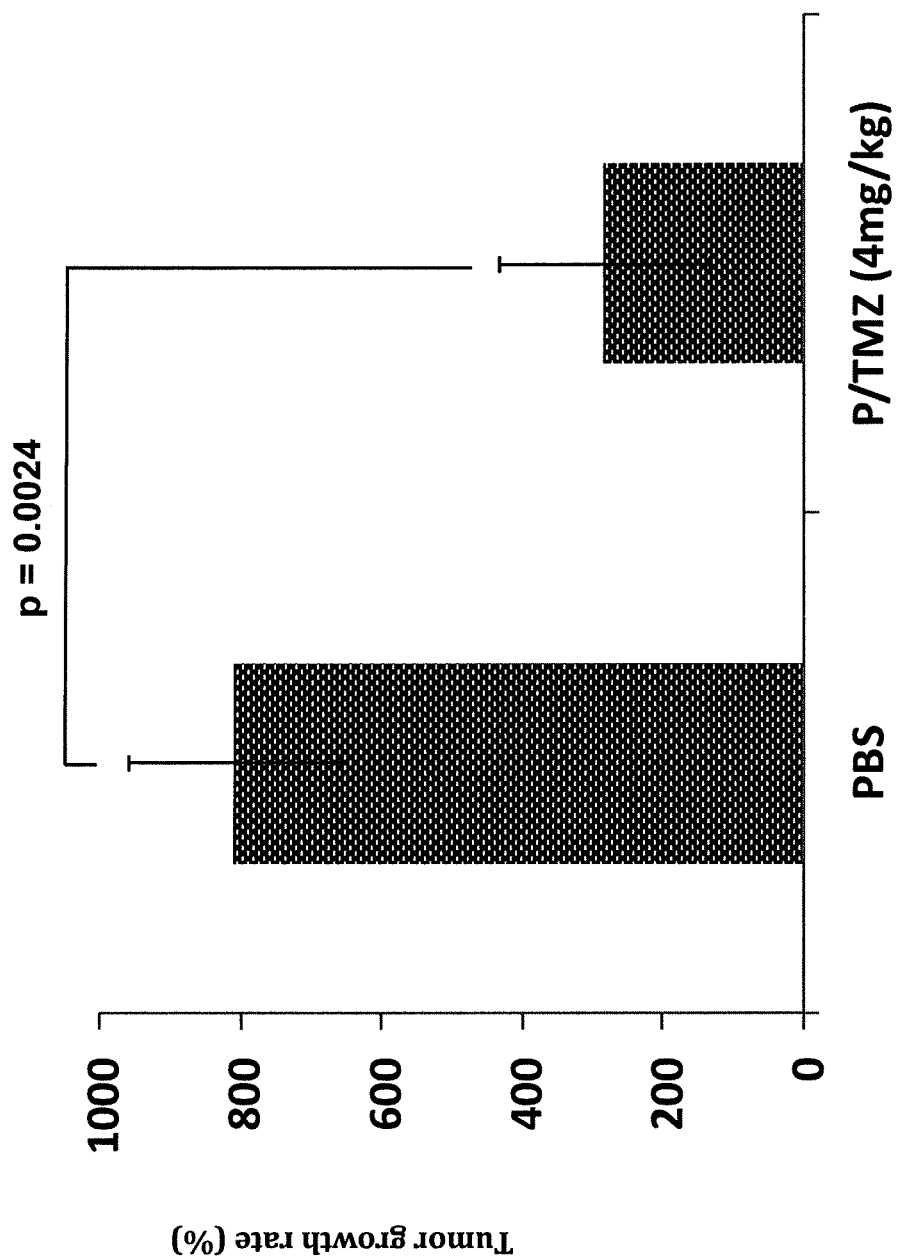
FIG. 12 depicts, in accordance with an embodiment herein, comparison of tumor growth rate between treated and untreated animals.
Figure 13:
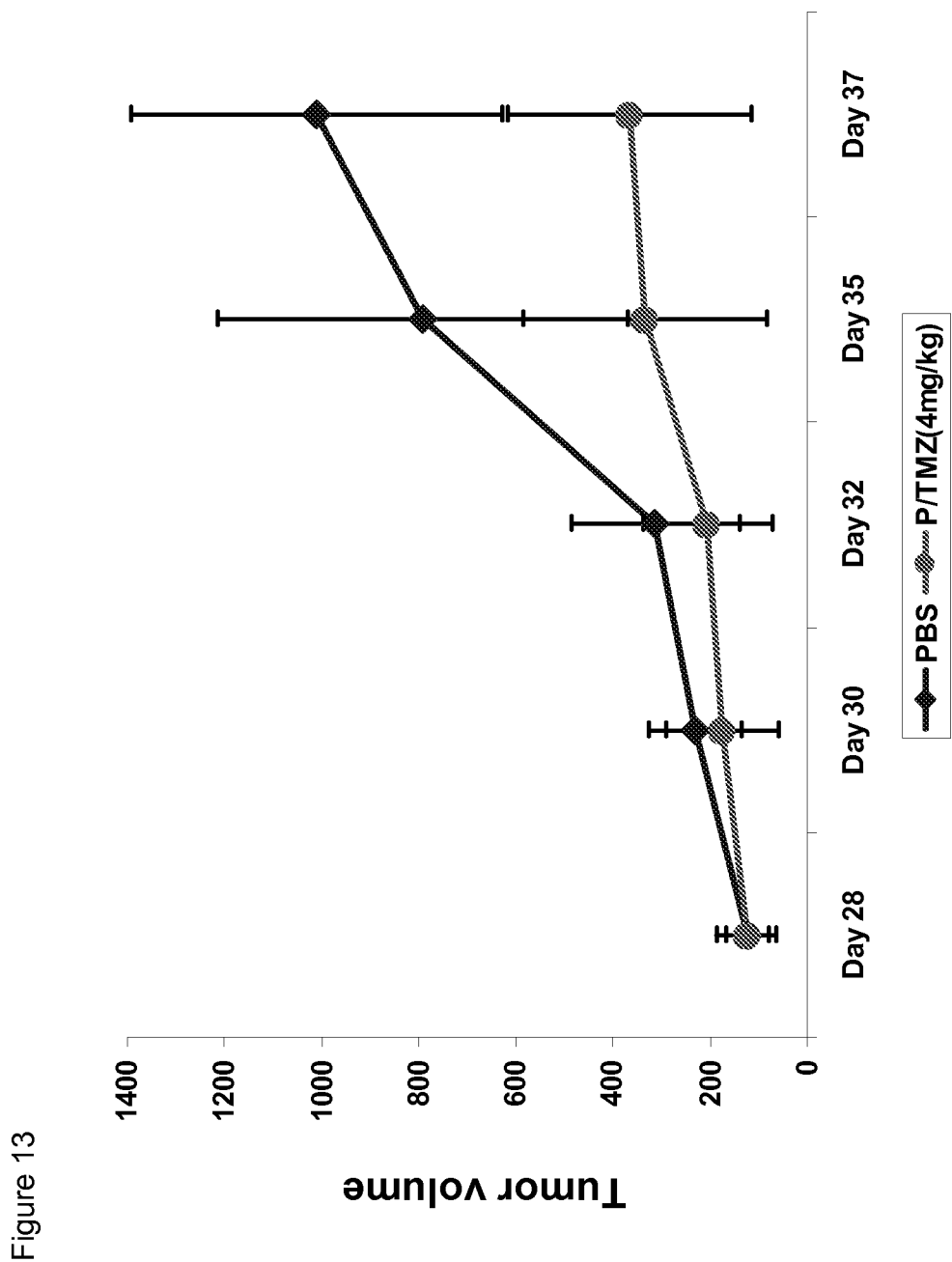
FIG. 13 depicts, in accordance with an embodiment herein, comparison of tumor volume between treated and untreated animals.

Treatment of animals with P/PEG(2%)/LLL(40)/TMZ (15%) {With 4 mg/kg of TMZ concentration} showed significant tumor growth inhibition compared with PBS treated animals. (p=0.0024, calculated from tumor growth rate as shown herein in FIG. 12). Temozolomide conjugate P/PEG(2%)/LLL(40)/TMZ(15%) at lower concentration (1 mg/kg of TMZ) did not achieve the desired effect. FIG. 13 illustrates the total tumor volume of different treatment groups.

Temozolomide nanoconjugate synthesized using polymalic acid as a platform significantly inhibited the tumor growth and proved its efficacy in vivo. Even without any active targeting, the nanoconjugate was effective.

Example 28

Temozolomide (TMZ) Dosage

FDA-approved dosage to treat patients in clinic using oral administration:

Newly Diagnosed High Grade Glioma:
75 mg/m$^2$ (corresponds to 2.3 mg/kg) daily p.o. for 42 days combined with focal radiotherapy followed by maintenance temozolomide for six cycles.

Maintenance Phase:
Cycle 1: 150 mg/m$^2$ (corresponds to 4.6 mg/kg) p.o. daily followed by 23 days without treatment.
Cycle 2 to 6: 200 mg/m$^2$ (corresponds to 6.15 mg/kg) p.o. daily followed by 23 days without treatment if toxicity does not occur.

In conjunction with various drug delivery systems described herein, TMZ can be administered via I.V. injection. As described herein, the inventors used mouse xenograft (U87MG, human glioma): 4 mg/kg intravenous injections for 5 consecutive days. As a result, the drug is less toxic because the direct tumor delivery and drug concentration in the tumor site is higher than after oral drug is administrated. TMZ covalently attached on polymer overcomes drug resistance.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. D. N. Louis, H. Ohgaki, 0. D. Wiestler, W. K. Cavenee, P. C. Burger, A. Jouvet, B. W. Scheithauer, and P. Kleihues. The 2007 WHO classification of tumours of the central nervous system. Acta Neuropathol. 114:97-109 (2007).
2. 2009 CBTRUS Statistical Report: Primary Brain and Central Nervous System Tumors Diagnosed in the United States in 2004-2005. http://www.cbtrus.org/reports/2009-NPCR-04-05/CBTRUS-NPCR2004-2005-Report-.pdf (accessed Nov. 17, 2009).
3. A. R. Asthagiri, N. Pouratian, J. Sherman, G. Ahmed, and M. E. Shaffrey. Advances in brain tumor surgery. Neurol Clin. 25:975-1003 (2007).
4. W. Stummer, U. Pichlmeier, T. Meinel, 0. D. Wiestler, F. Zanella, and H. J. Reulen. Fluorescence-guided surgery with 5-aminolevulinic acid for resection of malignant glioma: a randomised controlled multicentre phase III trial. Lancet Oncol. 7:392-401 (2006).
5. M. Lacroix, D. Abi-Said, D. R. Fourney, Z. L. Gokaslan, W. Shi, F. DeMonte, F. F. Lang, I. E. McCutcheon, S. J. Hassenbusch, E. Holland, K. Hess, C. Michael, D. Miller, and R. Sawaya. A multivariate analysis of 416 patients with glioblastoma multiforme: prognosis, extent of resection, and survival. J. Neurosurg. 95:190-198 (2001).
6. J. Arrowsmith, S. A. Jennings, D. A. Langnel, R. T. Wheelhouse, and M. F. Stevens. Antitumour imidazotetrazines. Part 39 synthesis of bis(imidazotetrazine)s with saturated spacer groups. J Chem Soc Perkin Trans 1. 24:4432-4438 (2000).
7. R. Stupp, W. P. Mason, M. J. van den Bent, M. Weller, B. Fisher, M. J. Taphoorn, K. Belanger, A. A. Brandes, C. Marosi, U. Bogdahn, J. Curschmann, R. C. Janzer, S. K. Ludwin, T. Gorlia, A. Allgeier, D. Lacombe, J. G. Cairncross, E. Eisenhauer, and R. O. Mirimanoff. Radiotherapy plus concomitant and adjuvant temozolomide for glioblastoma. N Engl J. Med. 352:987-996 (2005).
8. N. Auger, J. Thillet, K. Wanherdrick, A. Idbaih, M. E. Legrier, B. Dutrillaux, M. Sanson, and M. F. Poupon.

Genetic alterations associated with acquired temozolomide resistance in SNB-19, a human glioma cell line. Mol Cancer Ther. 5:2182-2192 (2006).
9. C. C. Chen, K. T. Kahle, K. Ng, M. Nitta, and A. D. Andrea. Of *escherichia coli* and man: understanding glioma resistance to temozolomide therapy. In E. G. Meir (eds.), CNS Cancer, Humana Press, Atlanta, 2009, pp 679-711.
10. G. J. Kitange, B. L. Carlson, M. A. Schroeder, P. T. Grogan, J. D. Lamont, P. A. Decker, W. Wu, C. D. James, and J. N. Sarkaria. Induction of MGMT expression is associated with temozolomide resistance in glioblastoma xenografts. Neuro Oncol. 11:281-291 (2009).
11. R. Satchi-Fainaro, M. Puder, J. W. Davies, H. T. Tran, D. A. Sampson, A. K. Greene, G. Corfas, and J. Folkman. Targeting angiogenesis with a conjugate of HPMA copolymer and TNP-470. Nat. Med. 10:255-261 (2004).
12. R. Duncan. The dawning era of polymer therapeutics. Nat Rev Drug Discov. 2:347-360 (2003).
13. S. V. Vinogradov, E. V. Batrakova, S. Li, and A. V. Kabanov. Mixed polymer micelles of amphiphilic and cationic copolymers for delivery of antisense oligonucleotides. J Drug Target. 12:517-526 (2004).
14. A. V. Kabanov, E. V. Batrakova, S. Sriadibhatla, Z. Yang, D. L. Kelly, and V. Y. Alakov. Polymer genomics: shifting the gene and drug delivery paradigms. J Control Release. 101:259-271 (2005).
15. D. Peer, J. M. Karp, S. Hong, 0. C. Farokhzad, R. Margalit, and R. Langer. Nanocarriers as an emerging platform for cancer therapy. Nat. Nanotechnol. 2:751-760 (2007).
16. M. Ferrari. Cancer nanotechnology: opportunities and challenges. Nat Rev Cancer. 5:161-171 (2005).
17. A. Nori, and J. Kopecek. Intracellular targeting of polymer-bound drugs for cancer chemotherapy. Adv Drug Deliv Rev. 57:609-636 (2005).
18. R. Duncan, M. J. Vicent, F. Greco, and R. I. Nicholson. Polymer-drug conjugates: towards a novel approach for the treatment of endrocine-related cancer. Endocr Relat Cancer. 12:S189-S199 (2005).
19. H. Maeda, J. Fang, T. Inutsuka, and Y. Kitamoto. Vascular permeability enhancement in solid tumor: various factors, mechanisms involved and its implications. Int Immunopharmacol. 3:319-328 (2003).
20. M. Fujita, B. S. Lee, N. M. Khazenzon, M. L. Penichet, K. A. Wawrowsky, R. Patil, H. Ding, E. Holler, K. L. Black, and J. Y. Ljubimova. Brain tumor tandem targeting using a combination of monoclonal antibodies attached to biopoly(b-L-malic acid). J Control Release. 122:356-363 (2007).
21. B. S. Lee, M. Fujita, N. M. Khazenzon, K. A. Wawrowsky, S. Wachsmann-Hogiu, D. L. Farkas, K. L. Black, J. Y. Ljubimova, and E. Holler. Polycefin, a new prototype of a multifunctional nanoconjugate based on poly(b-L-malic acid) for drug delivery. Bioconjug Chem. 17:317-326 (2006).
22. E. Segal, and R. Satchi-Fainaro. Design and development of polymer conjugates as anti-angiogenic agents. Adv Drug Deliv Rev. 61:1159-1176 (2009).
23. S. Brem, B. Tyler, K. Li, G. Pradilla, F. Legnani, J. Caplan, and H. Brem. Local delivery of temozolomide by biodegradable polymers is superior to oral administration in a rodent glioma model. Cancer Chemother Pharmacol. 60:643-650 (2007).
24. U. Akbar, T. Jones, J. Winestone, M. Michael, A. Shukla, Y. Sun, and C. Duntsch. Delivery of temozolomide to the tumor bed via biodegradable gel matrices in a novel model of intracranial glioma with resection. J Neurooncol. 94:203-212 (2009).
25. L. X. Zhao, J. L. Wang, X. P. Dai, Y. F. Wang, and Z. Z. Ji. Synthesis and antitumour activities of 3-substituted 4-oxo-3H-imidazo[5,1-d][1,2,3,5]tetrazine-8-carboxylic acids and their derivatives. Chin J Med. Chem. 11:263-269 (2001).
26. E. Holler, Poly(malic acid) from natural sources. In N. P. Cheremisinoff (eds.), Handbook of Engineering Polymeric Materials, Marcel Dekker, New York, 1997, pp. 93-103.
27. J. Carlsson, H. Drevin, and R. Axen. Protein thiolation and reversible protein-protein conjugation. N-Succinimidyl 3-(2-pyridyldithio)propionate, a new heterobifunctional reagent. Biochem J. 173:723-737 (1978).
28. J. Y. Ljubimova, M. Fujita, A. V. Ljubimov, V. P. Torchilin, K. L. Black, and E. Holler. Poly(malic acid) nanoconjugates containing various antibodies and oligonucleotides for multitargeting drug delivery. Nanomedicine. 3:247-265 (2008).
29. I. O. f. S. (ISO). Methods for Determination of Particle Size Distribution Part 8: Photon Correlation Spectroscopy, International Standard ISO 13321, 1996.
30. P. C. Hiemenz, Light scattering by polymer solutions, In P. C. Hiemenz (eds.), Polymer Chemistry: The Basic Concepts, Marcel Decker, New York, 1984, pp. 659-661.
31. F. N. Fu, and B. R. Singh. Calcein permeability of liposomes mediated by type A botulinum neurotoxin and its light and heavy chains. J Protein Chem. 18:701-707 (1999).
32. T. J. Mosmann. Rapid colorimetric assays for cellular growth and survival: application to proliferation and cytotoxicity assays. Immunol Methods. 65:55-63 (1983).
33. H. S. Friedman, T. Kerby, and H. Calvert. Temozolomide and treatment of malignant glioma. Clin Cancer Res. 6:2585-2597 (2000).
34. R. N. Trivedi, X. H. Wang, E. Jelezcova, E. M. Goellner, J. B. Tang, and R. W. Sobol. Human methyl purine DNA glycosylase and DNA polymerase b expression collectively predict sensitivity to temozolomide. Mol. Pharmacol. 74:505-516 (2008).
35. A. E. Nel, L. Madler, D. Velegol, T. Xia, E. M. Hoek, P. Somasundaran, F. Klaessig, V. Castranova, and M. Thompson. Understanding biophysicochemical interactions at the nano-bio interface. Nat. Mater. 8:543-557 (2009).
36. M. R. Lorenz, V. Holzapfel, A. Musyanovych, K. Nothelfer, P. Walther, H. Frank, K. Landfester, H. Schrezenmeier, and V. Mailander. Uptake of functionalized, fluorescent-labeled polymeric particles in different cell lines and stem cells. Biomaterials. 27:2820-2828 (2006).
37. D. E. Owens, and N. A. Peppas. Opsonization, biodistribution, and pharmacokinetics of polymeric nanoparticles. Int J. Pharm. 307:93-102 (2006).

What is claimed is:
1. A drug delivery system comprising a polymalic acid-based scaffold having a plurality of pendant carboxyl groups and at least one functional component conjugated to a pendant carboxyl group of the polymalic acid-based scaffold, wherein the at least one functional component includes temozolomide (TMZ) and the polymalic acid-based scaffold comprises a compound of the formula:

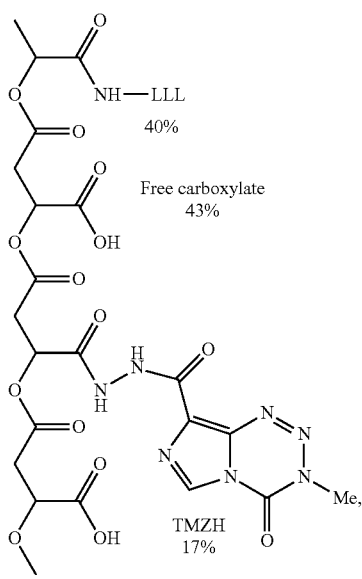

or a derivative thereof, wherein the derivative is an imidazotetrazine having antitumor activity.

2. The drug delivery system of claim 1, wherein the polymalic acid-based scaffold comprises a compound of the formula:

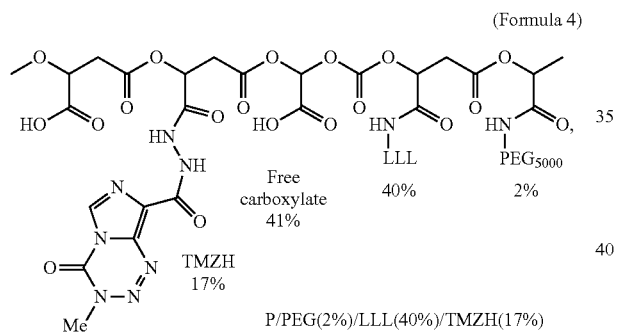

(Formula 4)

or a derivative thereof, wherein the derivative is an imidazotetrazine compound having antitumor activity.

3. A method of preparing a drug delivery system, comprising conjugating temozolomide hydrazide (TMZH) to an ionic polymalic acid, wherein TMZH is a compound of the formula:

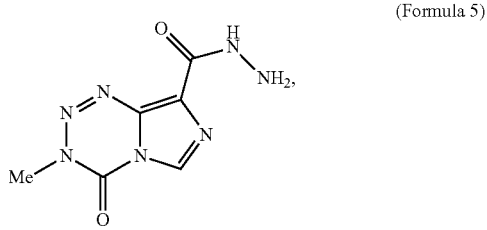 [SMILES: Cn1nnc2c(C(=O)NN)ncn2c1=O]

(Formula 5)

or a derivative thereof, wherein the derivative is an imidazotetrazine compound having antitumor activity, and wherein the ionic polymalic acid comprises a compound of the formula:

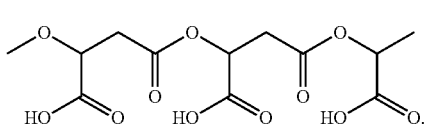

(Formula 2)

4. The method of claim 3, wherein the ionic polymalic acid comprises one or more antibodies.

5. The method of claim 4, wherein the one or more antibodies comprises an anti-TfR humanized antibody for transporting to a tumor.

6. The method of claim 3, wherein the ionic polymalic acid comprises a membrane disrupting unit.

7. The method of claim 6, wherein the membrane disrupting unit comprises trileucine (LLL) moiety, or LeuOEt (LOEt) moiety.

8. The method of claim 3, wherein the ionic polymalic acid comprises a polyethylene glycol (PEG) moiety.

9. A method of preparing a drug delivery system, comprising conjugating temozolomide hydrazide (TMZH) to an ionic polymalic acid, wherein TMZH is a compound of the formula:

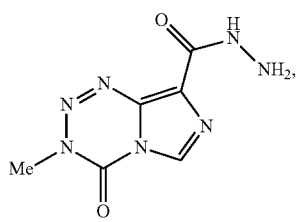

(Formula 5)

or a derivative thereof, wherein the derivative is an imidazotetrazine compound having antitumor activity, and wherein the ionic polymalic acid comprises a compound of the formula:

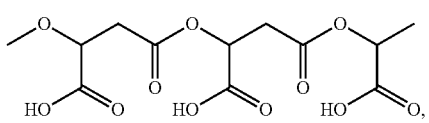

(Formula 2)

polyethylene glycol (PEG) moiety, and a membrane disrupting unit selected from trileucine (LLL) moiety, or LeuOEt (LOEt) moiety.

* * * * *

UNITED STATES PATENT AND TRADEMARK OFFICE
CERTIFICATE OF CORRECTION

| | | |
|---|---|---|
| PATENT NO. | : 9,629,919 B2 | Page 1 of 1 |
| APPLICATION NO. | : 15/054266 | |
| DATED | : April 25, 2017 | |
| INVENTOR(S) | : Patil et al. | |

It is certified that error appears in the above-identified patent and that said Letters Patent is hereby corrected as shown below:

In the Specification

In Column 1, Line 21, replace the Government Rights paragraph with the following:
--STATEMENT REGARDING FEDERALLY SPONSORED RESEARCH AND DEVELOPMENT
This invention was made with government support under Grant No. CA123495, awarded by the National Institutes of Health. The Government has certain rights in the invention.--

Signed and Sealed this
Third Day of September, 2024

Katherine Kelly Vidal
*Director of the United States Patent and Trademark Office*